(12) United States Patent
Fauver et al.

(10) Patent No.: US 6,959,130 B2
(45) Date of Patent: Oct. 25, 2005

(54) OPTICAL BEAM SCANNING SYSTEM FOR COMPACT IMAGE DISPLAY OR IMAGE ACQUISITION

(75) Inventors: Mark E. Fauver, Seattle, WA (US); Eric J. Seibel, Seattle, WA (US); Janet Crossman-Bosworth, Kenmore, WA (US)

(73) Assignee: University of Washington, Seattle, WA (US)

(*) Notice: Subject to any disclaimer, the term of this patent is extended or adjusted under 35 U.S.C. 154(b) by 0 days.

(21) Appl. No.: 11/074,241

(22) Filed: Mar. 2, 2005

(65) Prior Publication Data

US 2005/0173817 A1    Aug. 11, 2005

Related U.S. Application Data

(62) Division of application No. 10/763,896, filed on Jan. 23, 2004.
(60) Provisional application No. 60/442,852, filed on Jan. 24, 2003.

(51) Int. Cl.[7] ............................. G02B 6/26; C25F 3/00
(52) U.S. Cl. ........................... 385/25; 385/12; 385/31; 216/11
(58) Field of Search .......................... 385/147, 25, 31, 385/33, 12, 13, 901; 359/197–199, 209; 606/15, 606/16; 353/7; 250/234; 216/11; 438/31

(56) References Cited

U.S. PATENT DOCUMENTS

| | | | | |
|---|---|---|---|---|
| 4,234,788 A | * | 11/1980 | Palmer et al. | 250/227.26 |
| 6,515,274 B1 | * | 2/2003 | Moskovits et al. | 250/216 |
| 6,550,918 B1 | * | 4/2003 | Agostinelli et al. | 353/7 |
| 6,755,532 B1 | * | 6/2004 | Cobb | 353/7 |
| 6,779,892 B2 | * | 8/2004 | Agostinelli et al. | 353/7 |
| 6,845,190 B1 | * | 1/2005 | Smithwick et al. | 385/25 |
| 6,856,712 B2 | * | 2/2005 | Fauver et al. | 385/12 |
| 2002/0139920 A1 | * | 10/2002 | Seibel et al. | 250/208.1 |

* cited by examiner

Primary Examiner—Frank G. Font
Assistant Examiner—James P. Hughes
(74) Attorney, Agent, or Firm—Ronald M. Anderson

(57) ABSTRACT

An optical fiber having a reduced cross-sectional region adjacent to its distal end, which is fused to an optical component, is vibrated, rotating the optical component to scan a region. The optical component has a back focal point that is substantially coincident with an effective light source of the optical fiber, so that the light emanating from the optical component is either substantially collimated or convergent. The optical component is either a ball lens, a drum lens, a graded index lens, or a diffractive optical element. A vibratory node is also made substantially coincident with the back focal point of the optical component, producing a compact scanner with extensive field of view. The optical fiber is preferably reduced in cross-sectional area after the optical component is fused to the optical fiber, by immersion in a three-layer etch apparatus having an etch-stop layer, an etch layer, and a solvent layer.

15 Claims, 13 Drawing Sheets

SHORT FOCAL LENGTH $CO_2$ LASER LIGHT

DURING HEATING, GLASS MELT REGION MOVES ALONG FIBER

EXTREMELY LONG FOCAL LENGTH, EFFECTIVELY COLLIMATED

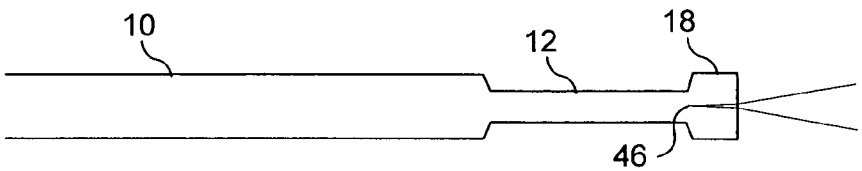

*FIG. 6A*

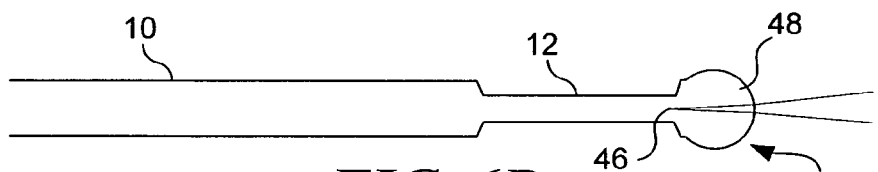

*FIG. 6B*

REDUCED DIVERGENCE ANGLE, BUT NOT COLLIMATED OR CONVERGING

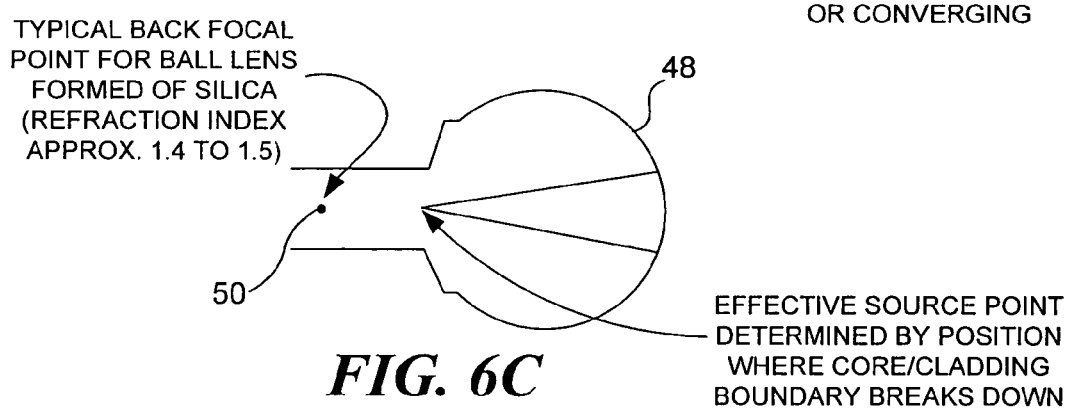

TYPICAL BACK FOCAL POINT FOR BALL LENS FORMED OF SILICA (REFRACTION INDEX APPROX. 1.4 TO 1.5)

EFFECTIVE SOURCE POINT DETERMINED BY POSITION WHERE CORE/CLADDING BOUNDARY BREAKS DOWN

*FIG. 6C*

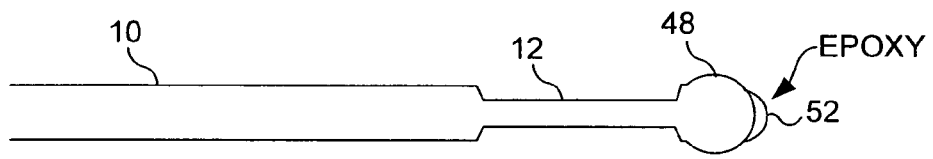

*FIG. 6D*

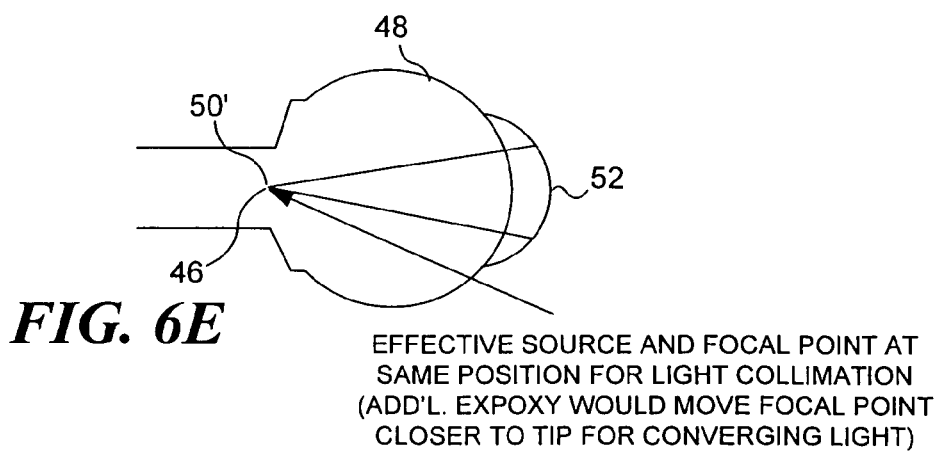

*FIG. 6E*

EFFECTIVE SOURCE AND FOCAL POINT AT SAME POSITION FOR LIGHT COLLIMATION (ADD'L. EXPOXY WOULD MOVE FOCAL POINT CLOSER TO TIP FOR CONVERGING LIGHT)

OPTICAL BEAM SCANNING SYSTEM FOR COMPACT IMAGE DISPLAY OR IMAGE ACQUISITION

RELATED APPLICATIONS

This application is a divisional application of prior copending application Ser. No. 10/763,896 filed Jan. 23, 2004, which itself is based on provisional application Ser. No. 60/442,852 filed Jan. 24, 2003 now abandoned, the benefits of the filing dates of which are hereby claimed under 35 U.S.C. §§ 119(e) and 120.

FIELD OF THE INVENTION

The present invention generally pertains to a relatively compact optical fiber beam scanning system and method for displaying or acquiring an image, and more specifically, relates to such a system in which a distal end of an optical fiber assembly is caused to resonantly rotate about a node when scanning, to display or acquire an image defined by its rotational angle.

BACKGROUND OF THE INVENTION

Most optical scanning applications use a moving mirror, either rotating or oscillating. A laser beam is typically projected onto the moving mirror so that the beam scans in a specified linear or two-dimensional (2-D) (raster) pattern at a frequency that is sufficient for the particular application. For optical displays, the field of view (FOV) is determined by the scanning amplitude and the particular optical design. There is a minimum frequency (rate) at which scanning displays need to be refreshed that is determined by the human perception of flicker from a scanned display. For ubiquitous raster scanning displays such as cathode ray tubes (CRTs) used in televisions and computer monitors, the display refresh rate is typically 30 Hz or more. Although a CRT is an electron-beam scanning electro-optical display, the same requirements for scan frequency and amplitude (in regard to the FOV) apply for all scanning displays. Thus, for a super video graphics array (sVGA) CRT resolution (i.e., 800 pixels×600 pixels), the minimum horizontal scan rates are 40 kHz for unidirectional scanning and 20 kHz for bidirectional scanning.

Combining both high resolution (i.e., an image with more than 400,000 pixels) and a relatively wide FOV (i.e., greater than 30°) in a single display is a difficult technical challenge, limiting the application of optical scanning for small-size, low cost optical scanners that have both high-resolution and wide FOV. There is a tradeoff between optical scanning frequency versus scanning amplitude (in regard to FOV) for all mirror-scanning devices. The faster the mirror scans, the greater the forces acting on the mirror. Such forces can deform the mirror surface, degrading image quality. This limitation is especially true for small, low-cost resonant mirror scanners. Rotating polygon mirror scanners can overcome this limitation or tradeoff between scan frequency and amplitude, but they are usually bulky, noisy, and costly. In the case of a resonant mirror scanner, the mirror cannot scan more than a few degrees in amplitude at frequencies of 20 kHz to 40 kHz, which is required for sVGA raster scanning displays. Since the optical beam reflects from the scanning mirror, the optical FOV is twice the total mirror deflection angle (i.e., FOV equals 2 times the mirror scan amplitude). However, at sVGA resolution and scan frequencies, an optical FOV on the order of 30 to 60° cannot be achieved using a low-cost resonant mirror scanner to produce micro-displays.

Accordingly, it will be apparent that a different approach to optical scanning is needed to produce both an acceptable resolution and FOV within a compact assembly. The device should also be low in cost and relatively simply to produce.

SUMMARY OF THE INVENTION

In consideration of the problems with the prior art as discussed above, an alternative method of optical scanning at both high amplitudes and frequencies (in regard to FOV) has been experimentally verified at the University of Washington. This new method provides for scanning a micro-fabricated optical waveguide, not a mirror, at mechanical or vibratory resonance. The waveguide is preferably in a fixed-free cantilever configuration, with a distal (free) end of the waveguide swinging at a resonant amplitude that is equivalent to the optical FOV. Thus, the scanning micro-fabricated waveguide has much smaller mass, inertia, and viscous drag than a scanning micro-electromechanical system (MEMS) mirror of 1 mm square. Furthermore, the optical surface of the waveguide is typically less than 10 microns in diameter (at the distal tip) versus MEMS mirror sizes that are at least 50 to 100 times larger. Due to the smaller size of the optical surface on a resonant scanning waveguide compared to the planar mirror surface of resonant mirror scanners, the deterioration of the optical surface is expected to be slower and the lifetime of the waveguide scanner to be longer. The geometry of the resonant waveguide scanner is cylindrical, which is an ideal form for mounting within spectacle frames for micro-displays and within slender tubes for micro-image acquisition systems (endoscopes and bore scopes). Prototype fiber scan systems are expected to be no greater than 2 mm in diameter. However, it should be understood that the present invention also encompasses an embodiment of an optical beam scanner in which a portion (preferably a majority) of the scanning occurs with light emitted from an optical component at the distal end of the waveguide, due to rotation, while another portion of the scanning is the result of a translation of the optical component and distal end of the waveguide. Such an embodiment may be useful where there is less need for the more compact waveguide scanner that results from scanning by rotation, with little or no translation occurring proximate the distal end of the scanning waveguide.

In addition to its ultra-thin diameter, another major advantage of the micro-fabricated optical waveguide over mirror-based resonant optical scanners is its simplicity of design, fabrication, and assembly/packaging. Accordingly, the resonant waveguide optical scanner is extremely low cost in both fabrication and material unit costs. By comparison, the multiple actuators that drive a mirror-based system are complex in design and fabrication, whereas a single cheap actuator is all that is needed to drive a cantilevered portion of the custom waveguide into its resonant scanning patterns. In addition, a mirror scanner has the disadvantage of requiring optical alignment with the illuminating light source or optical fiber, whereas the custom optical waveguide can be micro-fabricated at the end of the optical fiber itself, so that additional optical coupling and alignment are unnecessary.

Finally, the micro-fabricated waveguide scanner can include an integrated micro-optical lens system for specific optical scanning applications, so that the optical waveguide is referred to as a "lensed optomechanical waveguide" or simply as a "lensed waveguide." For example, high-resolution optical scanning may be achieved with a microlens attached directly to the distal end of the waveguide scanner. The microlens both collimates the emerging optical beam and adds mass to the distal tip. The point where the light exits the small core of the waveguide and enters the optical component is the effective point source or the "effective light source" of the distal microlens. At modes of resonance greater than the fundamental, the added mass moves the vibratory node very close to the distal tip of the waveguide near the effective light source of the microlens. The vibratory node is then substantially coincident with this effective light source position that is rotated by the angular deflection of the distal region of the lensed waveguide to scan an optical beam of light.

More specifically, one aspect of the present invention is directed to a compact scanner that includes a waveguide for conveying light between a proximal and a distal end. The waveguide includes a region of substantially reduced cross-sectional area that is disposed adjacent to the distal end of the waveguide. The optical component is attached to the distal end of the waveguide and has a back focal point. An actuator is included for exciting the region of substantially reduced cross-sectional area of the lensed waveguide to vibrate at a desired frequency and in a desired pattern. The optical component and the waveguide are configured so that a vibratory node of the waveguide is substantially coincident with the back focal point of the optical component. Accordingly, the vibration of the waveguide in the region of substantially reduced cross-section causes the optical component to rotate about a substantially fixed point to scan a region. Light exiting the optical component preferably travels in either a convergent or a collimated path, toward the region to be scanned.

In a preferred embodiment, the waveguide comprises an optical fiber. The region of substantially reduced cross-sectional area is preferably etched to reduce the cross-sectional area of that region relative to adjacent portions of the waveguide that are not reduced in cross-sectional area. The reduction in cross-sectional area of the portion that is cantilevered enhances lateral bending of the waveguide. Also, the optical component is preferably fused to the distal end of the waveguide, i.e., to a portion of the waveguide that is not substantially reduced in cross-sectional area. Optionally, the region of substantially reduced cross-sectional area may be formed to be linear or to have a desired nonlinear shape.

As noted above, an effective source of the light that is conveyed through the waveguide corresponds to a position adjacent to the distal end of the waveguide where the waveguide is no longer internally guiding light. In at least some embodiments, the effective light source position is preferably substantially coincident with the back focal point of the optical component and with the vibratory node of the waveguide. Those of ordinary skill in this art will understand that in an optical fiber waveguide, light is no longer guided through an optical fiber from a point adjacent to its distal end where its small-core-cladding boundary has been removed; in the following discussion, this point corresponds to the effective light source position of the optical fiber.

The compact scanner may further include a scan lens disposed between the optical component and the region being scanned. The scan lens optically modifies the light exiting the optical component that is incident on the region being scanned.

Preferably, the optical component comprises either a ball lens, a drum (barrel) lens, or a graded index lens (also often called a "gradient index" lens, or as referred to herein—a GRIN lens), although other types of optical components might instead be used, such as a diffractive optical element.

A spacer can be used for coupling the optical component to the distal end of the waveguide. The spacer is sized to make the vibratory node of the waveguide substantially coincident with the effective light source at the distal end of the waveguide. This position of the effective light source may also be substantially coincident or proximal to the back focal point of the optical element to achieve high field of view imaging.

In a preferred embodiment, the actuator excites the region of substantially reduced cross-sectional area to vibrate at a resonance frequency. For example, the waveguide may be excited into a second resonant mode.

Another aspect of the present invention is directed to a method for fabricating a compact optical scanner for scanning a region. The method includes the steps of providing a waveguide through which light is guided between a proximal end and a distal end of the waveguide. An optical component having a back focal point is attached to the distal end of the waveguide. A cross-sectional area of a portion of the waveguide adjacent to the distal end is then substantially reduced, leaving the distal end of the waveguide where the optical component is attached unaffected. An actuator is coupled to the waveguide to vibrate the portion of waveguide that is reduced in cross-sectional area at a desired frequency and in a desired pattern. Excitation of the waveguide by the actuator causes the optical component to rotate without substantial lateral displacement, so as to scan a region with light exiting the optical component.

Still another aspect of the present invention is directed to a method for scanning a region with light conveyed through a waveguide between a proximal end and a distal end. The waveguide has a portion that is reduced in cross-sectional area disposed adjacent to the distal end, and an optical component is attached to the distal end of the waveguide. The method includes the steps of actuating the portion of the waveguide that is reduced in cross-sectional area to vibrate at a desired frequency and in a desired pattern, and controlling a dimensional configuration of the waveguide so as to ensure that the effective light source of the optical component is substantially coincident with a vibratory node of the waveguide. The optical component is thereby caused to rotate about a generally fixed point when the waveguide is vibrating, so that light exiting the optical component scans the region as the optical component rotates.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 5A:
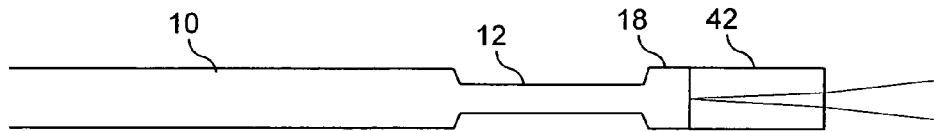
Figure 5B:
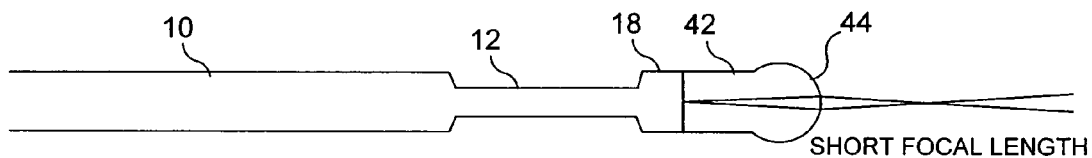
Figure 5C:
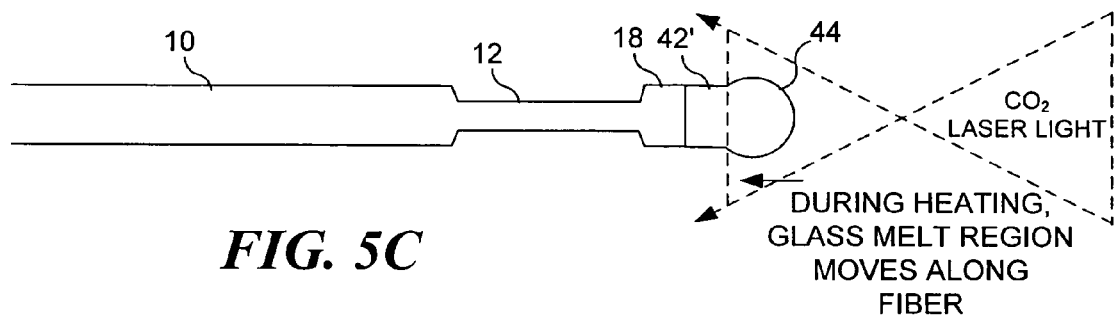
Figure 5D:
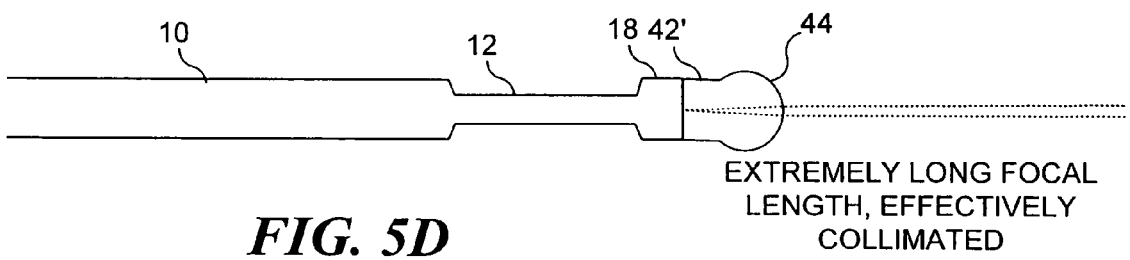
Figure 7A:
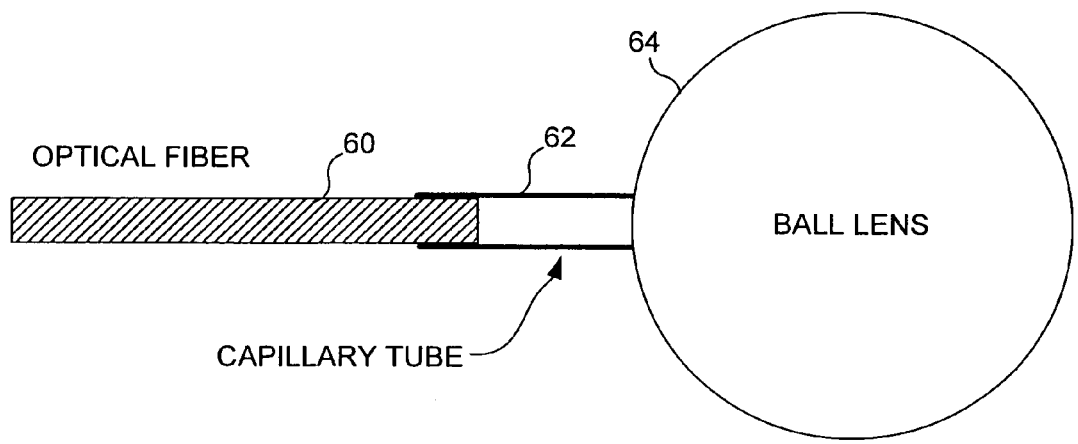
Figure 7B:
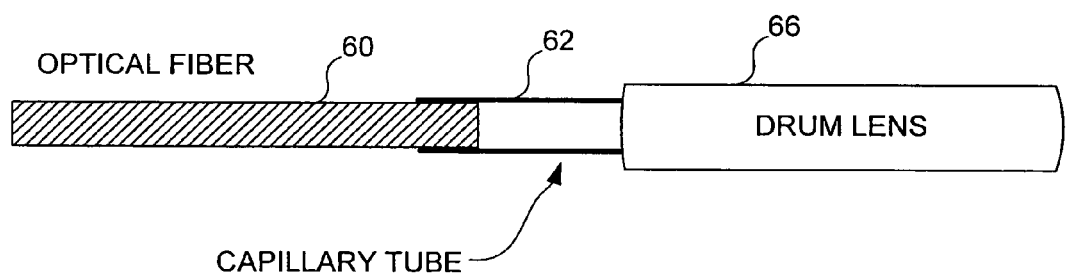
Figure 8:
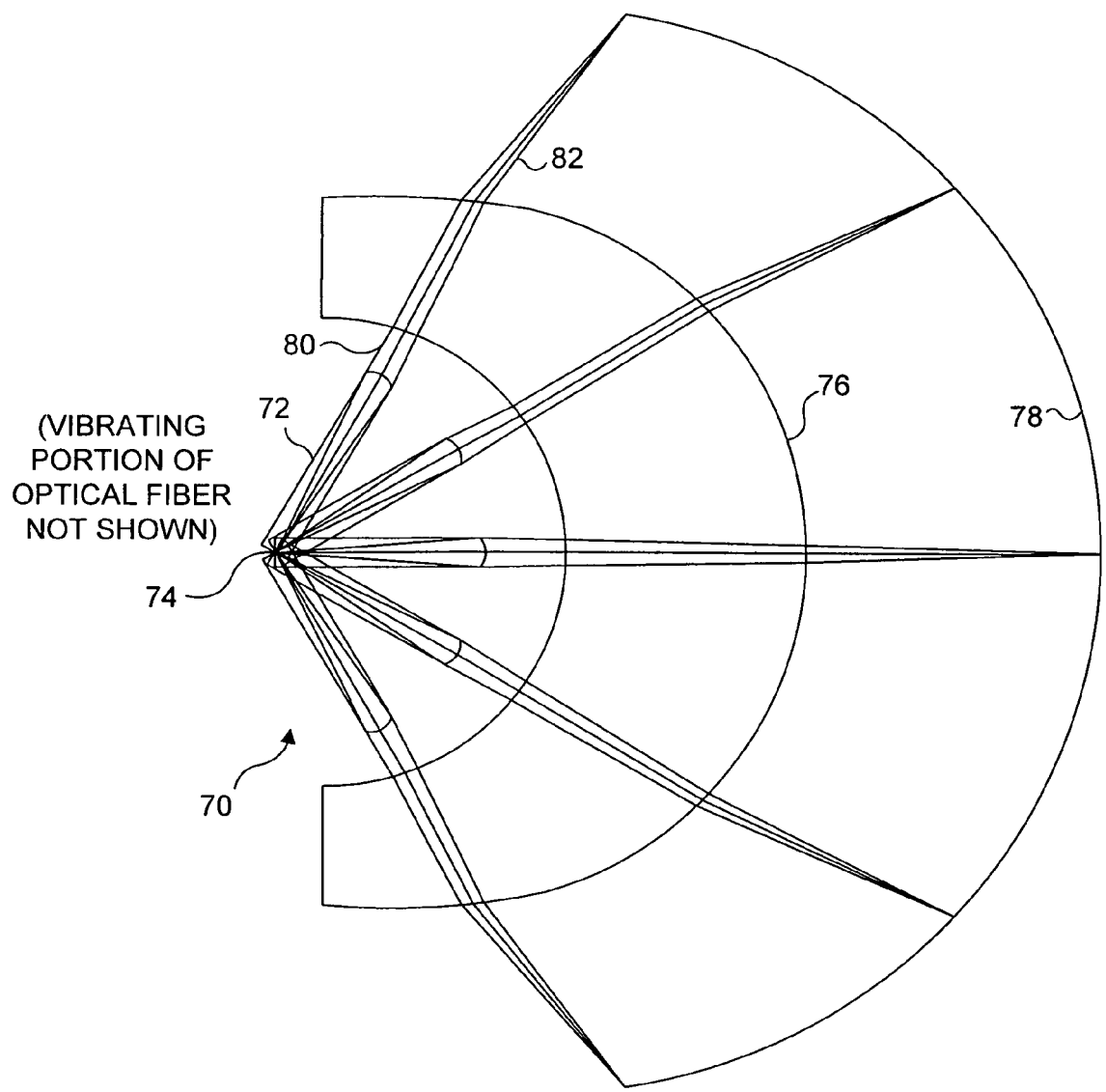
Figure 9:
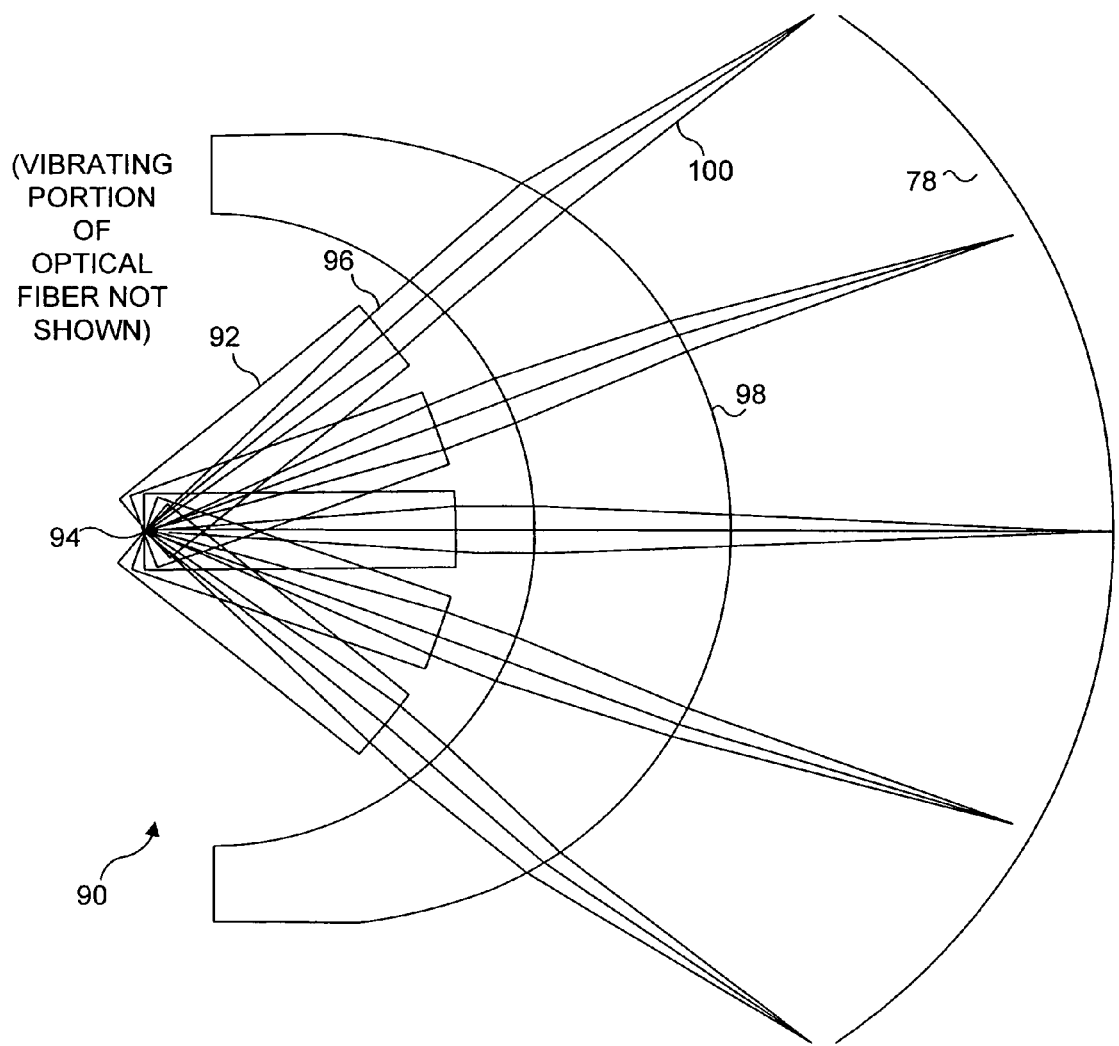
Figure 10A:
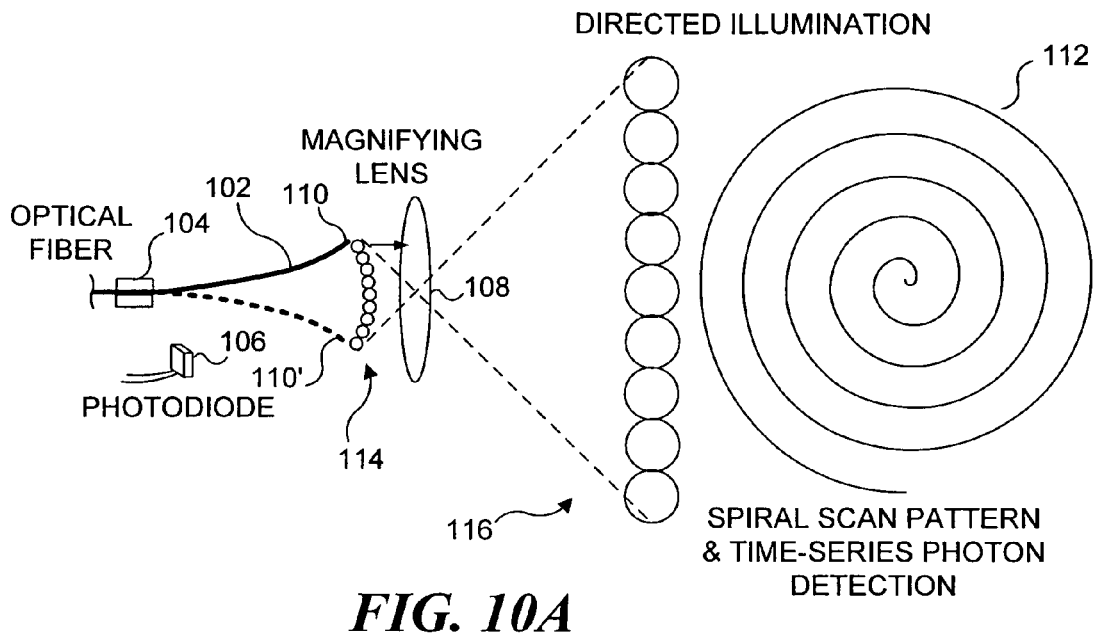
Figure 10B:
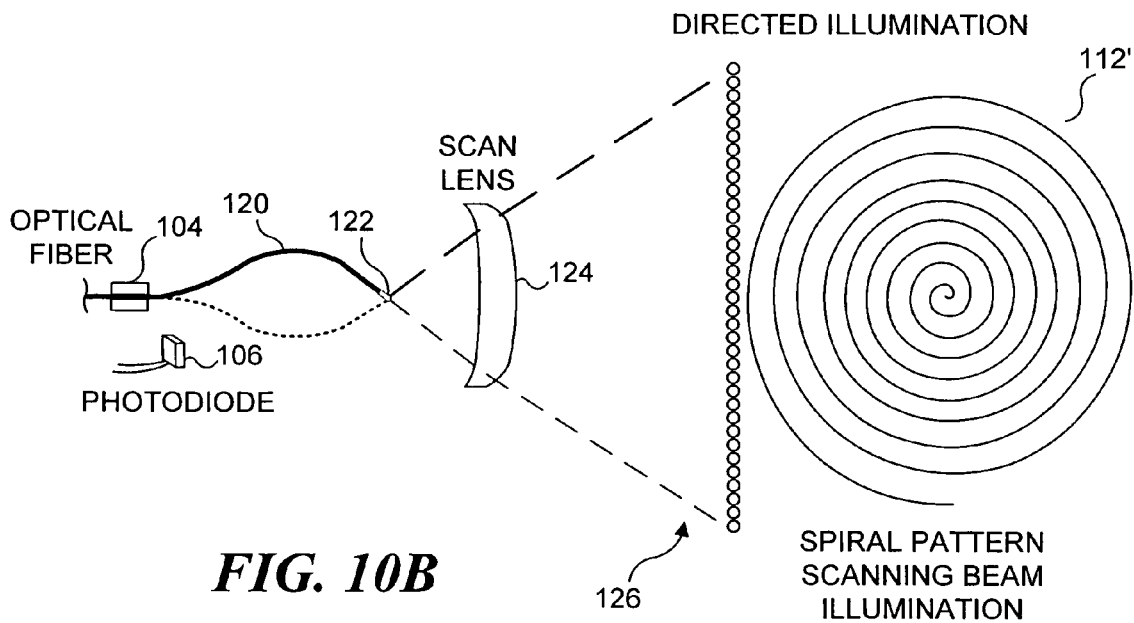
Figure 11A:
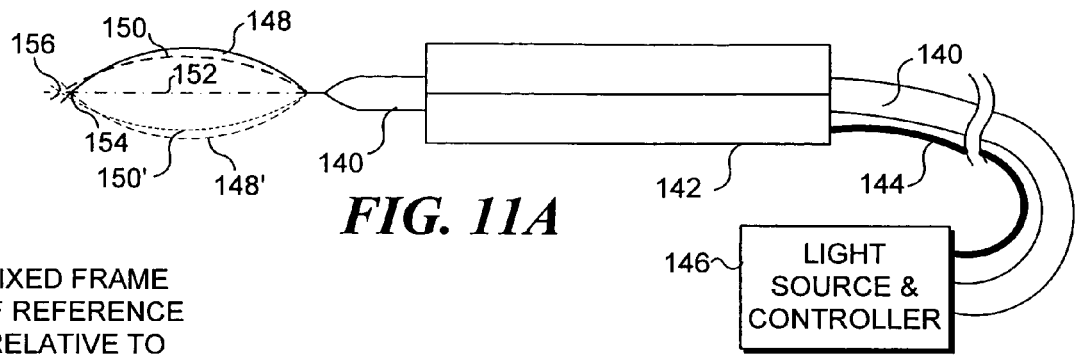
Figure 11B:
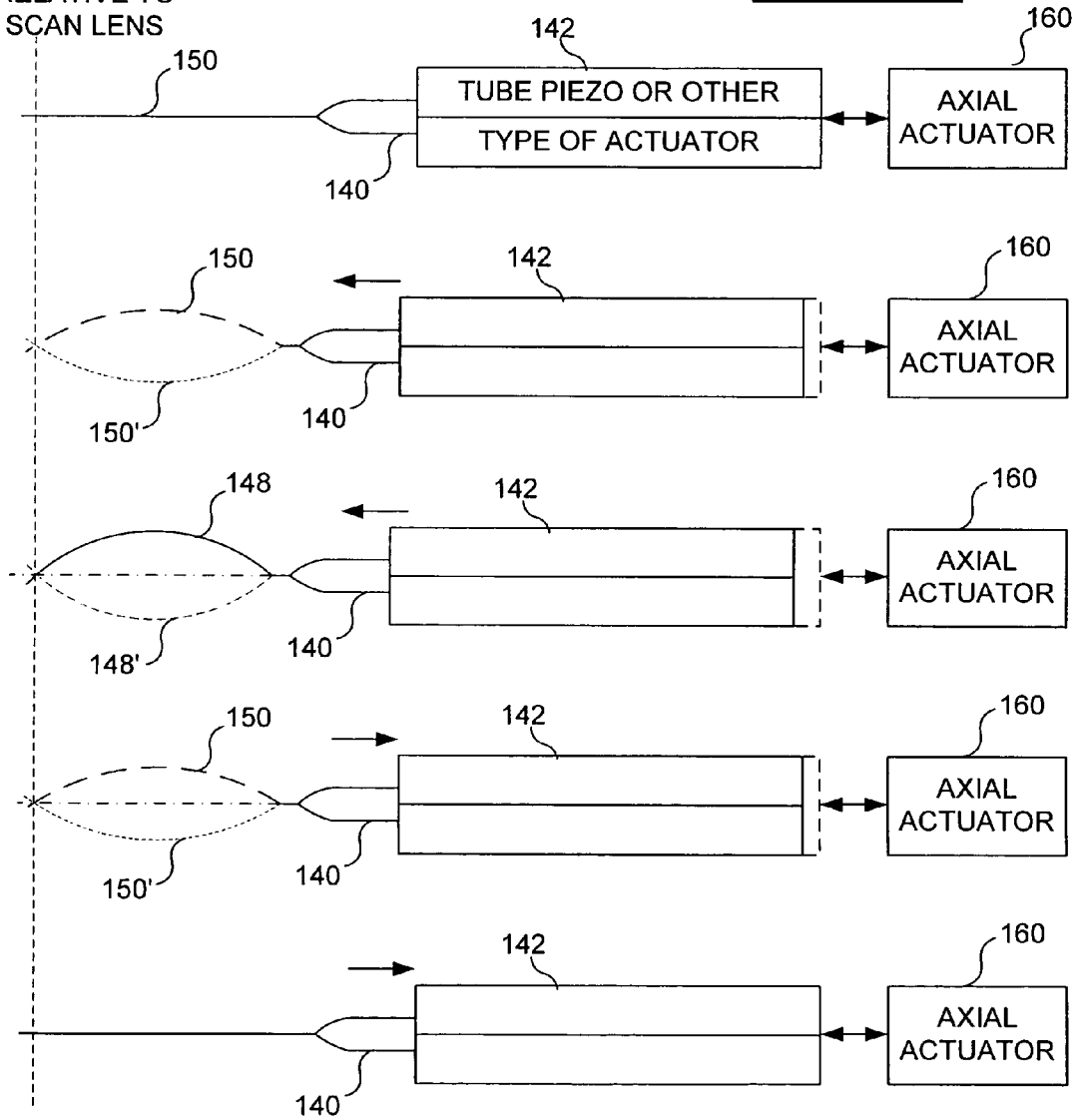
Figure 12A:
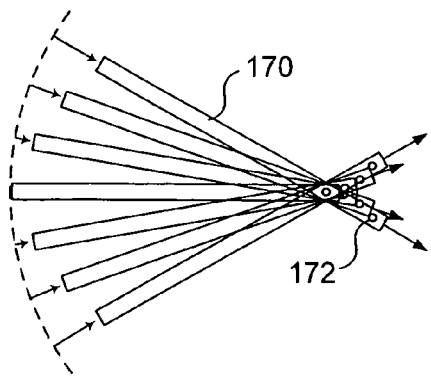
Figure 12B:
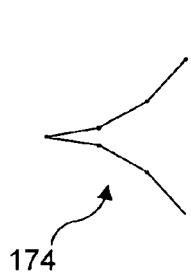
Figure 12C:
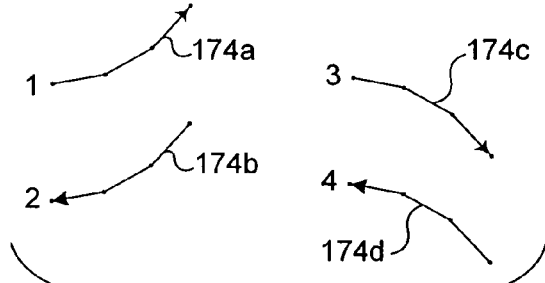
Figure 12D:
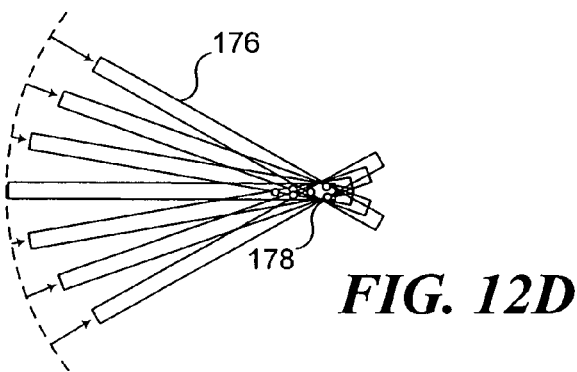
Figure 12E:
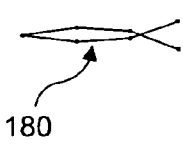
Figure 12F:
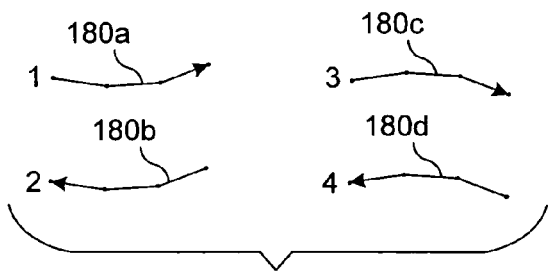
Figure 13:
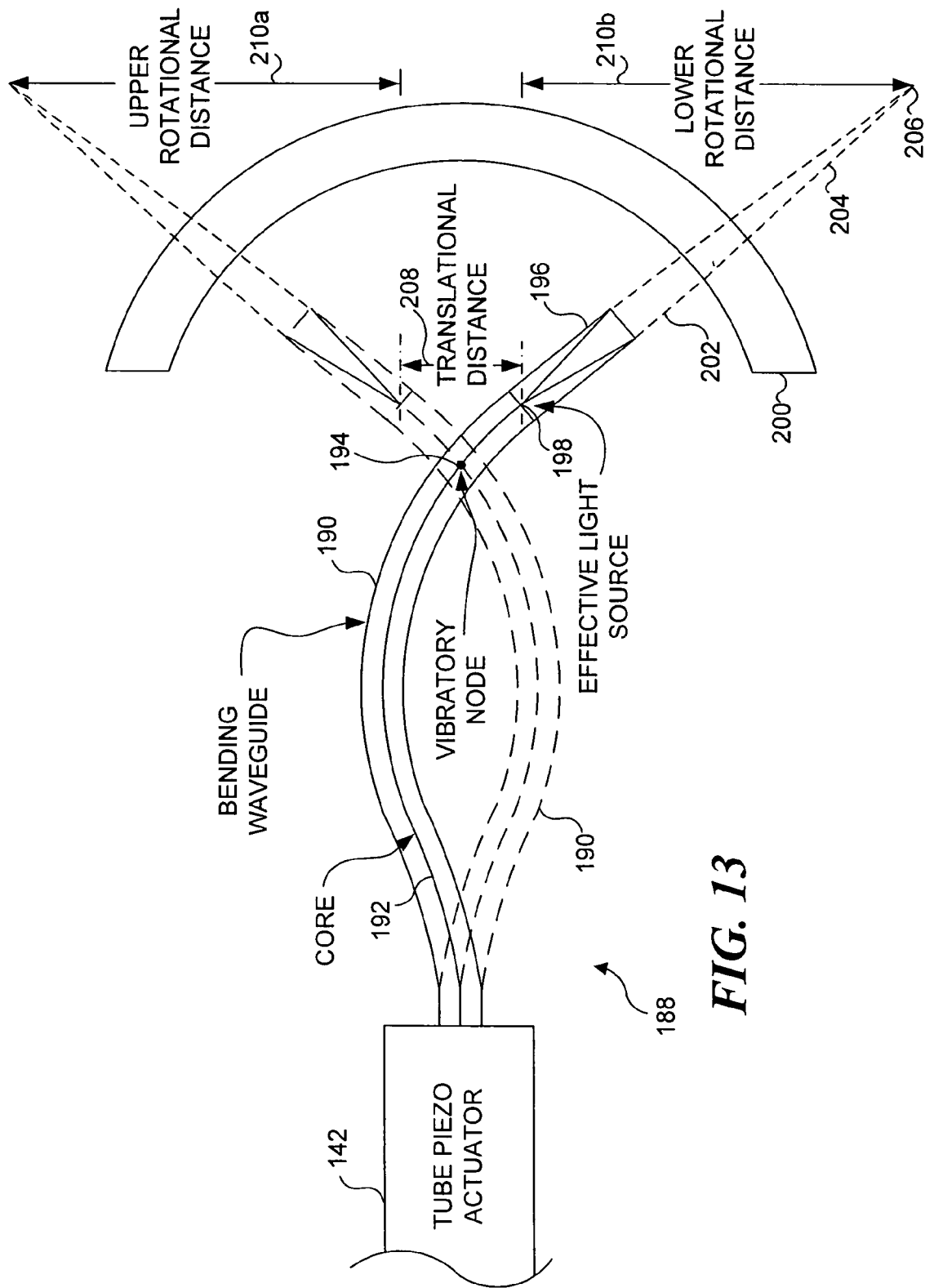

FIG. 5A schematically illustrates a distal end of a three-layer etched single mode optical fiber to which a short multimode section has been fused;

FIG. 5B is a schematic diagram illustrating a ball lens with a relatively short focal length that has been created at the tip region of an optical fiber using a carbon dioxide laser or other heat source;

FIG. 5C is a schematic diagram showing how during heating, a glass melt region moves longitudinally along the optical fiber, FIG. 5D is a schematic diagram illustrating a ball lens with an extremely long focal length (effectively collimated) that has been created at the tip region of an optical fiber;

FIG. 6A is a schematic view of an optical fiber with an etched middle section created using the three-layer etch technique;

FIG. 6B shows how application of heat to the tip of the optical fiber of FIG. 6A has been used to create a ball lens at the tip region;

FIG. 6C is an enlarged view of the ball lens in FIG. 6B;

FIG. 6D illustrates a small volume of epoxy that has been added to the distal end of the ball lens on the optical fiber of 6C;

FIG. 6E is an enlarged view of the ball lens with added epoxy of FIG. 6D;

FIG. 7A is a schematic view of an optical fiber coupled to a ball lens and including a short section of capillary tubing;

FIG. 7B is a schematic view of an optical fiber coupled to a drum (e.g., a GRIN) lens and including a short section of capillary tubing;

FIG. 8 is a schematic diagram showing how a wide FOV is provided due to a 5 degree convergence angle produced at the distal end of a multimode optical fiber, which is fused to a single mode optical fiber (or at the distal end of a drum lens with curved distal surface that is fused to a single mode optical fiber), the converging light being further focused by a scan lens;

FIG. 9 is a schematic diagram showing how a GRIN lens attached is used to produce collimated light over a wide FOV by the present invention, the collimated light being focused by a scan lens;

FIG. 10A (Prior Art) illustrates a scanning optical fiber in which the distal end of the optical fiber is caused to move in a desired pattern, such as a spiral scan, to scan a region with light that is imaged by a magnifying lens;

FIG. 10B illustrates how the present invention scans in a desired pattern, such as a spiral scan, by vibrating the optical fiber to rotate an optical element disposed at the distal end, to scan a region with relatively high resolution;

FIG. 11A schematically illustrates an optical fiber scanner system in accord with the present invention, showing how an increased amplitude produces a small variation in an axial position of the effective light source position of light at the distal end of the optical fiber;

FIG. 11B schematically illustrates how an axial actuator is used to compensate for the axial offset of the effective light source relative to the vibratory node of an optical fiber;

FIGS. 12A–12C schematically illustrate the trajectory followed by the effective light source position as an optical fiber vibrates, when the effective light source is coincident with the vibratory node (when the optical fiber is at its rest orientation);

FIGS. 12D–12F schematically illustrate the trajectory followed by the effective light source position as an optical fiber vibrates, when the effective light source is offset slightly toward the distal end relative to the vibratory node to reduce the lateral error; and FIG. 13 is a schematic diagram of another embodiment of an optical beam waveguide scanner in accord with the present invention, wherein an optical component and the distal end of the waveguide experience translation to scan a region as well as scanning the region as a result of rotation of the optical component.

DESCRIPTION OF THE PREFERRED EMBODIMENT

Construction of a Scanning Optical Fiber

Figure 1A:
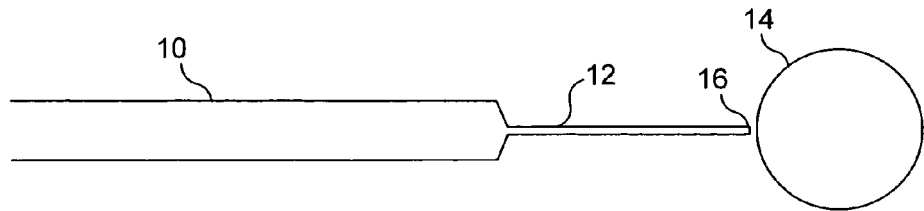
FIG. 1A is a schematic diagram illustrating how attachment of a larger optical component to the distal end of an optical fiber is difficult due to a limited area of contact between the optical fiber tip and the optical component.

When using fusion splicing for joining an optical fiber to optical components (e.g., to a GRIN lens or larger core multimode optical fiber), it is preferable to carry out any etching of the optical fiber after the fusion splicing has been completed, because it is easier to work with the optical fiber during the fusion process before it is made more flexible by being etched to a reduced diameter. Optical fiber scanning applications rely on the reduced diameter and mass distributions along the optical fiber to produce a relatively wide FOV at video rate scan frequencies. However, the extremely small (e.g., about 10–50 microns) diameter of a distal tip 16 of an etched region 12 on an optical fiber 10 (typically single mode) makes the attachment of added optical components, such as a ball lens 14, to distal tip 16 difficult, as will be apparent from the example shown in FIG. 1A. Optical fiber scanning applications frequently require optical beam conditioning to produce collimated light emitted by the scanner, or use of a different exit numerical aperture (NA) than the optical fiber would normally have. Since the light exiting commercial optical fibers is diverging from the core (NA=0.11 is typical for single mode optical fibers), the goal for a fiber-based optical beam scanner is to reduce the exit NA. NA is equal to the refractive index of the medium (typically air) where the light is traveling after leaving the optical fiber times the sine of the maximum half-angle of the light rays either entering or exiting the lens. Although not customary, the functional relationship between NA and the sine of the angle to a lens of a specific focal length does allow the resulting NA to equal zero for collimating light that is exiting a lensed waveguide. In addition, it should be noted that a further reduction in NA for the lensed waveguide will result in an optical beam of light that is converging, with NA becoming negative as the sign of focal length changes from positive to negative. Thus, by making the effective light source position at the distal end of the waveguide coincident with the back focal point of the optical component, the resulting optical beam is collimated (i.e., NA=zero). By making the effective light source position more proximal in position relative to the back focal point of the optical component, the resulting optical beam will be converging, further reducing NA of the lensed waveguide (NA defined as being negative).

Figure 1B:
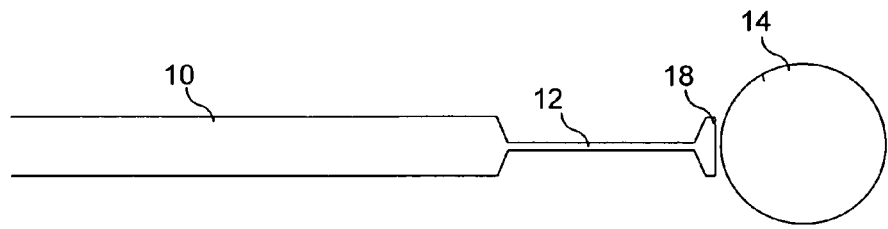
FIG. 1B is a schematic diagram illustrating use of a three-layer etched fiber with an unetched distal end, which facilitates attachment of an optical component to the optical fiber.

A new etching technique has been developed in connection with the present invention that enables optical fibers to be etched in region 12, but leaves a tip 18 at the initial diameter (e.g., at a diameter of 125 microns), as shown in FIG. 1B. The configuration in FIG. 1B makes possible the attachment of lenses, including GRIN lenses and ball lenses, or other optical fibers (such as a multimode optical fiber) to the tip of an etched optical fiber. However, in the case where epoxy is used for adhesively joining the optical component to the optical fiber, the etching step is usually done prior to the epoxy adhesion because the chemicals used in the etch process may degrade the epoxy bond between the optical fiber and the optical component.

A multimode fiber may be fused onto a single mode optical fiber, since the multimode optical fiber provides the option of forming a refractive or diffractive lens surface at the distal tip, creating a drum (barrel) refractive lens or a diffractive optical element. This configuration has the advantage of having a small core size along most of the vibrating length of an optical fiber scanner, so that the diameter can be reduced and optimal dynamic properties can be achieved without sacrificing the wave guiding ability of the optical fiber. At the junction between single mode and multimode fibers, the light freely diverges from this effective light source through the multimode section at the distal end, filling out a lens created at the very distal end of this form of hybrid optical fiber scanner. Since the proposed microfabrication of the single mode optical fiber enables the fusion of preexisting (commercially available) lens stock to the optical fiber to be done beforehand, standard procedures of fusing GRIN lenses can be incorporated into the process of making the lensed waveguide.

Figure 1C:
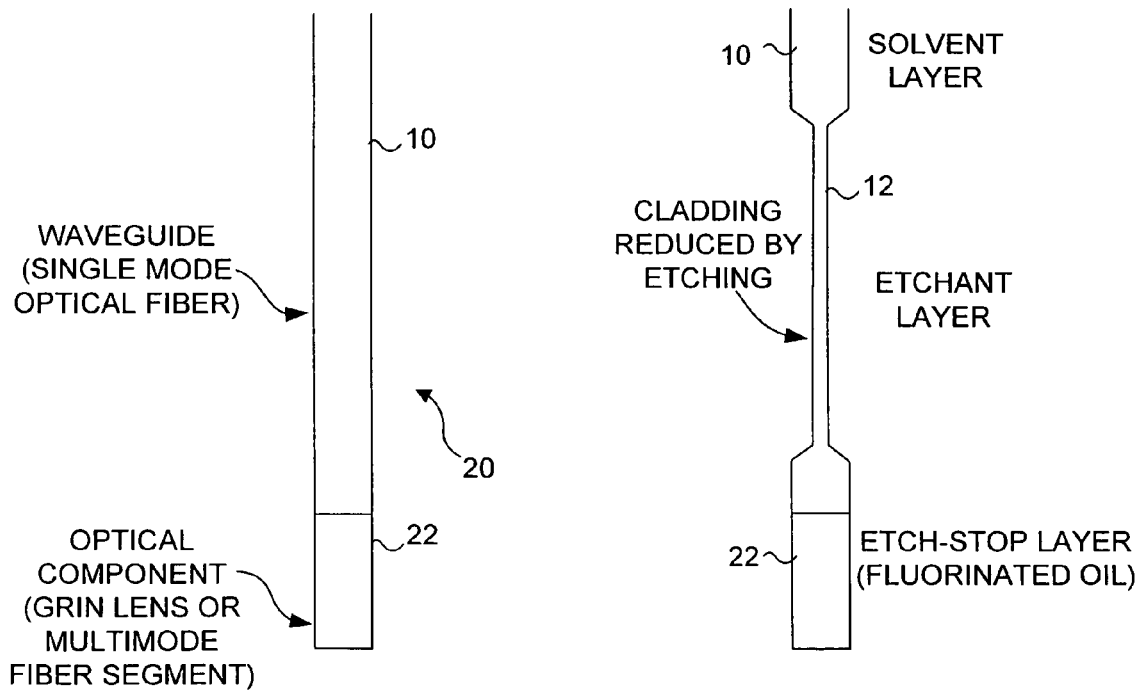
FIG. 1C is a schematic diagram showing a lensed waveguide that is specifically a GRIN lens (or alternatively, a multimode fiber segment) that has been attached to a conventional 125 micron diameter single-mode optical fiber using commercial fusing equipment.
Figure 1D:
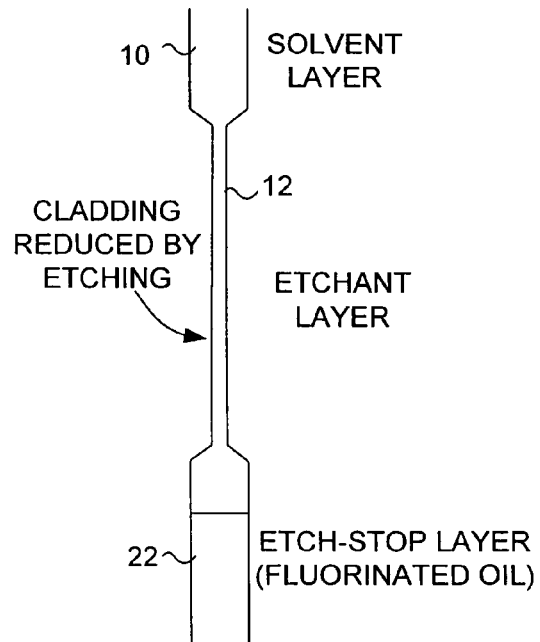
FIG. 1D is a schematic diagram showing an optical component that has previously been fused to an optical fiber (as in FIG. 1C) and subsequently reduced in diameter at a mid-section by three-layer acid etching.

As shown in FIGS. 1C–1D, an optical fiber scanner in accord with the present invention is preferably constructed from single mode optical fiber 10 having a 125 micron cladding diameter and a 3–4 micron core diameter. The first step is to attach a GRIN lens 22 or multimode optical fiber segment (or other optical component) to the distal end of optical fiber 10, creating a lensed waveguide 20. Next, a three-layer etch technique is employed to produce a fiber profile as shown in FIG. 1D. In this Figure, the cladding on the optical fiber is etched away to substantially reduce the cross-sectional area of a portion of the single mode optical fiber by immersing a region 12, which is adjacent to the distal end to which the GRIN lens 22 or the multimode fiber segment is attached, in an etchant layer, as described below.

Figures 2A, 2B:
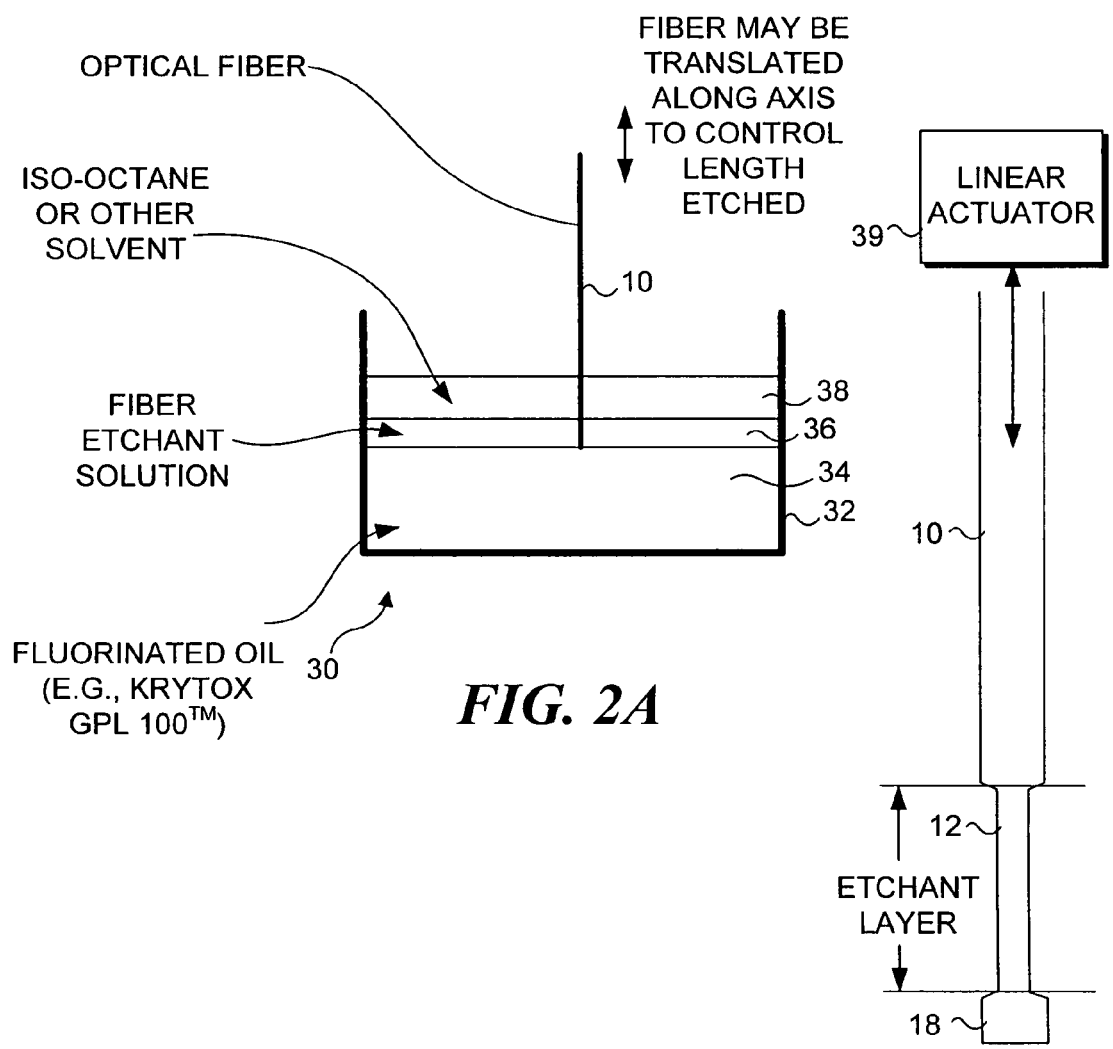
FIG. 2A is a schematic illustration apparatus usable for three-layer etching.
FIG. 2B is a greatly enlarged view of an optical fiber that has been three-layer etched using the apparatus of FIG. 2A.

FIG. 2A shows details of a three-layer etch apparatus 30 that is used to etch a region of an optical fiber 10 to reduce its cross-sectional area. An exemplary optical fiber that etched in the three-layer etching apparatus is shown in FIG. 2B. As will be apparent from this example, the optical fiber can be etched over a longer longitudinal portion by moving the optical fiber longitudinally during the etching process.

Three-layer etch apparatus 30 includes a chamber 32 holding (from the bottom layer to the top layer) an etch-stop layer 34, an etchant layer 36, and a solvent layer 38. Etchant layer 36 preferably comprises hydrofluoric (HF) acid. Solvent layer 38 is preferably iso-octane, which confines the upper etch boundary to the meniscus layer formed between the solvent and the etchant layers, by preventing etchant vapors from attacking any part of the optical fiber that is not submerged into etchant layer 36. Solvent layer 38 is not miscible with the HF acid that is preferably used for etchant layer 36. The bottom or etch-stop layer 34, which is more dense than the other liquid layers and is immiscible or non-reactive with the etchant, acts as an etch stop mask. Fluorinated oils, such as Krytox GPL 100™, work well for the etch stop layer, because they are unreactive with HF acid, do not harm an optical fiber, and the residue of such oils on the optical fiber can easily be removed with a solvent after the etching is completed. When using a 48% concentration HF acid as the etchant, etch times to reduce the diameter of optical fiber 10 from 60 microns to 10 microns range from about 20 minutes to about 34 minutes. An etched 10 micron diameter region on the optical fiber still has enough cladding for efficient wave guiding.

In a preferred method, etch chamber 32 is at first partially filled with a fluorinated oil, such as Krytox GPL 100™. Care should be taken to ensure the cleanliness of the optical fiber prior to etching, and that the cleave of the optical fiber is uniform, since it is important for the fluorinated oil mask to uniformly wet the optical fiber. After the optical fiber is inserted in the mask liquid etch-stop layer to the desired depth (typically a 0.4 mm to 2 mm), a predefined quantity of the etchant (e.g., HF acid —48% concentration) is added to achieve a depth of etchant layer 36 that is sufficient to provide the desired length of etch region 12 along the longitudinal axis of optical fiber 10. Iso-octane or another solvent is then added to produce solvent layer 38 immediately above etchant layer 36, to eliminate any etching by HF acid vapor, limiting the etch region to the depth of the HF liquid layer (ignoring meniscus effects). After the etch of the optical fiber is completed, the optical fiber is removed from the three-layer etch apparatus, and any remaining fluorinated oil is removed with an appropriate solvent (such as Vertrel XF™). As noted above, a linear actuator 39 can be coupled to optical fiber 10, to move more of the optical fiber into the etchant layer during the etching process, to extend the length of etched region 12 beyond the depth of the etchant layer 36.

A $CO_2$ laser (e.g., a Synrad™ laser operating at 10 watts and having a 1.5" focal length) provides a convenient method for trimming the optical fiber tip to fine-tune its resonant frequency and vibratory node position. The optical fiber is suspended vertically and driven at its base using a piezoelectric driver that operates at the desired resonant frequency. As the silica is melted (removed or redistributed), the amplitude response of the optical fiber increases. The melting process is halted when the maximum response (or at least a specified amplitude or scan angle response) is achieved. Depending on the optical beam conditioning requirements, care must be taken to use heat settings and pulse times for the $CO_2$ laser that are appropriate for achieving the desired radius of curvature of the distal end of the optical fiber. Use of a high heat setting (i.e., about 9.5 watts) at an extended pulse time (i.e., about 1 ms–10 ms) for the laser produces a relatively large melt region, thereby creating a ball end with a diameter 2–3 times larger than the initial optical fiber diameter. Use of a shorter pulse time (<<1 ms) leads to a thinner melt region and forms a larger radius of curvature at the optical fiber end. Because of the tight focal point and highly divergent $CO_2$ laser beam, positioning of the optical fiber tip in the $CO_2$ laser light greatly influences the results obtained with the laser settings listed above. It is recommended that the optical fiber be positioned well above (i.e., a few mm above) the laser beam to enable more uniform heating of the optical fiber across its end face.

Readily available fusing equipment may be employed to attach optical components to the end of an etched optical fiber that will then be used as a scanner. However, the more preferred procedure is to first fuse a lens component onto the distal end of an optical fiber and then etch only region 12 of the optical fiber (i.e., adjacent to its distal end), while preserving the optical properties of the microlens or other optical component fused thereon, as indicated by the examples in FIGS. 1C and 1D. The advantage of attaching the lens component before implementing the three-layer etching process is that commercial fusion splicers are designed for use with long lengths of standard and consistent diameter, such as optical fibers of 125 micron diameter.

Figure 3A:
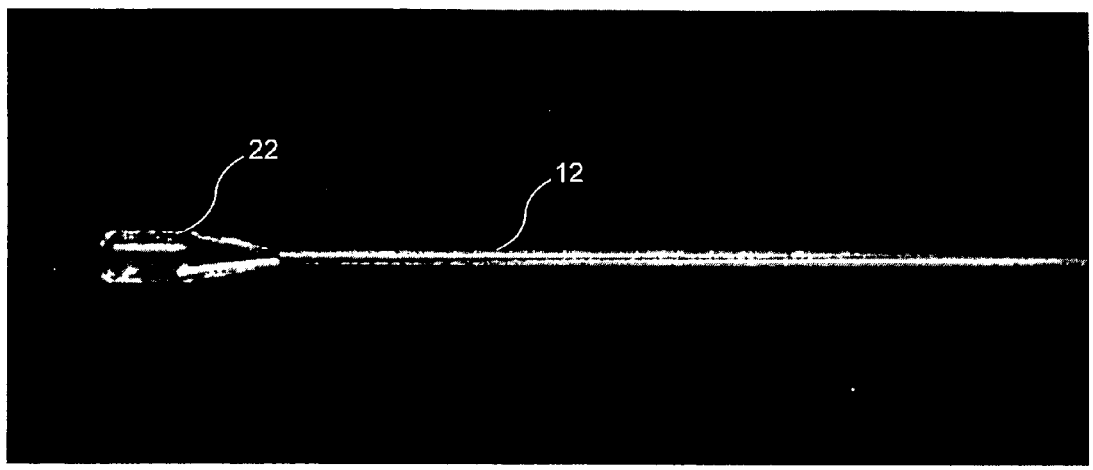
FIG. 3A is a photomicrograph of a tip of a three-layer etched optical fiber.
Figure 3B:
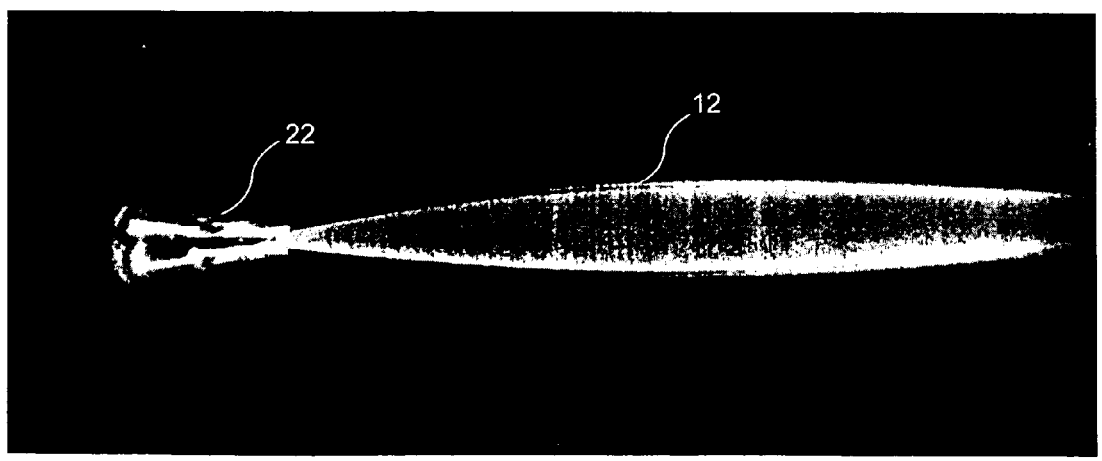
FIG. 3B is a photomicrograph of the tip of the three-layer etched optical fiber of FIG. 3A, where the reduced diameter portion is vibrating at about 10 KHz.

FIG. 3A shows a photomicrograph of an optical fiber after it has undergone the three-layer etch process to produce etched region 12, where the original 125 micron outer diameter of the optical fiber has been preserved at the distal tip, to which a GRIN lens 22 is fused. In FIG. 3B, the etched region 12 of the optical fiber is shown vibrating at about 10 kHz. This three-layer etching process is characterized by a mechanical and chemical low impact on the optical fiber, so that delicate structures are not compromised.

Figure 4:
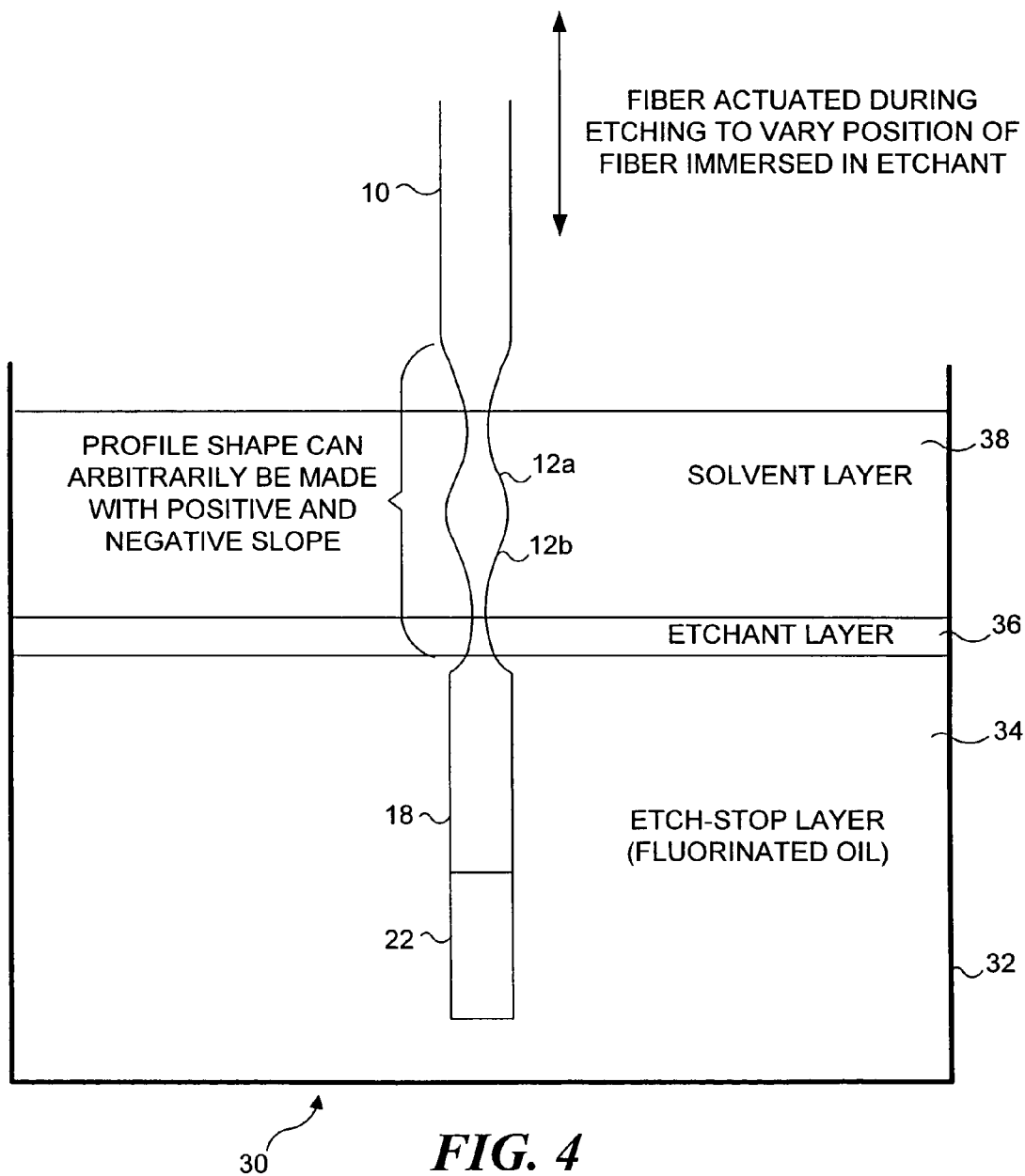
FIG. 4 is a schematic diagram of the apparatus of FIG. 2A, illustrating how an optical fiber can be moved longitudinally, to control profile shape of the etched portion of the optical fiber.

A second advantage of the three-layer etch process is its ability to create arbitrary positive and negative slope etch profiles on an optical fiber. FIG. 4 shows an optical fiber that is translated along its longitudinal axis through etchant layer 36 to produce an arbitrarily-shaped profile that includes a positive slope portion 12a and a negative slope portion 12b. The sharpness of curvature of the profile is limited by the heights of the meniscus layers (at each boundary) and the depth of etchant layer 36.

The three-layer etch apparatus enables three separate liquid layers and the optical fiber immersed in these liquids to be visibly perceived. A double window (not shown) on etch chamber 32 enables control of the illumination light to facilitate visualizing the distinction between the three liquids (which all appear clear to the naked eye), as well as visualizing the optical fiber position while it is immersed in the liquids comprising the three layers. Phase contrast or polarization microscopy is useful in distinguishing between the liquid layers in the chamber and the optical fiber. This system also enables real-time monitoring of the etch rate, visual inspection of the optical fiber including control over the length of fiber immersed in the liquid etch-stop layer, and verification of the height of the etchant layer.

Other masking techniques could be used. For example, a fluoropolymer coating can be applied to protect the tip region of the optical fiber during the etching procedure, which has the advantage of enabling dynamic etching (i.e., moving the optical fiber along its longitudinal axis during the etch) while still maintaining the initial fiber diameter for a short region at the tip of the optical fiber.

Table 1, below, shows data regarding maximizing the angular deflection of the tip by varying the amount etched from the cross-sectional area of the optical fiber.

TABLE 1

| Diameter d# (in microns) after Etching the Optical Fiber | | Second Resonance Mode Freq. (Hz) | Tip Angular Deflection (deg.) {max. full cone angle} |
| --- | --- | --- | --- |
| $d_1$ | 70.9 | 4,370 | 17 |
| $d_2$ | 59 | 4,090 | 28 |
| $d_3$ | 52 | 3,710 | 44 |
| $d_4$ | 38 | 2,946 | 49 |
| $d_5$ | 24 | 2,027 | 53 |
| $d_6$ | 12 | 1,187 | 33 |

TABLE 1-continued

One attractive design for creating an optical fiber scanner with a lens is to employ a multimode optical fiber for extending the distance the light travels from the effective light source beyond the wave guide limits of the optical fiber. Where the cladding has been removed or is not present on the optical fiber adjacent to its distal tip, the optical fiber ceases to provide a waveguide function. That point where the waveguide function ceases is referred to as the effective light source position of the optical fiber scanner, which is also conjugate to the proximal end of the waveguide. A multimode fiber 42 that is fused to the distal end 18 of optical fiber 10 is shown in FIG. 5A. The light exiting the multimode optical fiber diverges, instead of being collimated or converging, as preferred. However, multimode optical fiber 42 can be heated with a $CO_2$ laser or other heating method to create a ball lens 44 on one end, as illustrated in FIG. 5B. Thus, the multimode fiber serves to lengthen the distance between the effective light source distal tip 18 and the distal surface of ball lens 44, which is important, because the $CO_2$ laser method, if applied to heat the original optical fiber instead of the multimode optical fiber to form a ball lens, will position the effective light source position too close to the distal surface of the ball lens, so that only a slight reduction in divergence angle is obtained. By properly matching the length of the section of multimode fiber 42 to the focal length of a ball lens 44 (or other optical component), a much greater reduction in NA of the lensed waveguide can be achieved, as shown in FIG. 5B, which has a converging beam of relatively short focal length. The length of the multimode section can be increased further to provide focusing of a larger diameter beam of projected light to a smaller focal spot closer to the lensed waveguide, possibly eliminating the need for a scan lens. A further advantage of this method is that the added mass due to the lens is minimized, since the $CO_2$ laser-heated multimode optical fiber forms a drum lens without the extra mass of a full sphere. This use of a drum lens reduces the scan frequency and field of view for optical fiber scanning applications.

The positioning of the back focal point of the lens relative to the effective light source may be altered by changing the time length of exposure of the end of the multimode fiber section to the $CO_2$ laser light (or other heating method), which enables the exit angle of the light to be fine tuned, e.g., to achieve an extremely long focal length that is effectively collimated, as shown in FIGS. 5C and 5D. A drum or GRIN lens is attached to a three-layer-etched fiber in a similar manner.

If the index of refraction of the existing optical fiber can be changed, for example, by diffusing (doping) another element into the glass at the tip of the single mode fiber so that the index is close to 2.00, then the $CO_2$ laser or other heating method can suffice for creating a ball lens that at least collimates, if not focuses, the light exiting the assembly.

The epoxy spinning method used to form lenses, as described in copending commonly assigned patent application Ser. No. 09/994,377, filed on Nov. 26, 2001, may be readily applied to modify existing lenses formed at the tip of an optical fiber scanner, by $CO_2$ laser machining to fine tune the focal length and radius of curvature, extend the lens to allow larger optical beams, and reduce lens aberrations (e.g., chromatic aberration). This method enables real-time monitoring of the projected light spot shape and size (and divergence/convergence angle), which makes it relatively easy to compensate for unexpected optical irregularities.

FIGS. 6A–6E show the use of the three layer etch method to create large diameter section 18 on the distal end of an etched optical fiber 10 and then using a $CO_2$ laser to create a ball lens 48 on the end. Note that the tip region can be etched to any desired diameter (less than the initial diameter) to prepare the tip for subsequent heating. The diameter of the tip determines the possible range of ball lens diameters formed during heating (as small as the etched diameter, to approx 2–3 times larger). Heating methods, such as those using $CO_2$ laser machining, tend to eliminate the core/cladding index of refraction difference, so the light no longer waveguides, but instead travels freely from an effective light source position 46 through the modified glass region that has been heated and machined with the laser. Because a back focal point 50 of the ball lens shown in FIG. 6C is not aligned with effective light source position 46, the epoxy spinning method is employed to add a small amount of lens material 52 to ball lens 48 (without the problems of off-axis center-of-mass that tend to occur when using only epoxy to form the lens) in an adjustable manner, so that the back focal point of the ball can be matched to or made coincident with the effective light source position 50' as shown in FIGS. 6D and 6E, to produce a collimated output beam (not shown). The volume of delivered epoxy may be controlled by pipetting, and it is critical to apply this in a uniform manner so that the epoxy wets the ball lens on the tip of the optical fiber symmetrically. The wetting properties of the glass can be altered through silanization or other surface treatments to change the hydrophobicity of the surface; these alterations can greatly affect the shape and extent to which the epoxy adheres to the silica The epoxy spinning apparatus enables adjustment of the epoxy droplet shape to produce the desired convergence/divergence angle of light exiting the added material through variation of the spin speed, which determines the centrifugal force applied to the epoxy droplet.

In all of these methods, when using a second mode resonance for a fiber-based optical scanner, it is important to position the effective light source position within the optical fiber substantially at the second vibrational node, which is near the tip of the optical fiber, so that an optical scanner is produced in which the effective light source only rotates but does not translate through an arc to implement scanning. The use of a rotating effective light source and optical component has advantages, especially when employing external optics (e.g., one or more scan lenses) for further optical beam conditioning, since the light appears to be angularly scanned in two-dimensions from a single location in space instead of from a source that is moving in an arc, as in the prior art.

For applications requiring a large exit angle of light from the optical fiber, a light scattering tip could be made by bubbling air or depositing small reflective particles into optical epoxy, and then using the epoxy spinner to adjust this deposit in place on the end of the optical fiber. Another approach (not shown) would be to create a reduced aperture size by etching down through the core/cladding boundary of the optical fiber, and then depositing a metal such as aluminum or some other thin coating on the optical fiber that is not light transmissive to cause the light exiting the optical fiber to diffract, thereby increasing the exit angle of the light.

FIGS. 7A and 7B show the use of a spacer 62 to produce an air gap between the distal end of a single mode optical fiber 60 and a ball lens 64 (FIG. 7A) or a drum lens 66 (FIG. 7B). A capillary tube serves as spacer 62 for this purpose, providing the advantage of a lower index of refraction between the optical fiber and lens, and enabling two refractive surfaces to act on the light emitted from the optical fiber.

The use of external lenses that are not attached to the distal end of the waveguide and which are referred to herein as "scan lenses," are shown in FIGS. 8–9. These designs show examples where a non-translating light source feeds a low convergence angle optical beam and a collimated optical beam, respectively, into one (or more) external scan lenses. An additional scan lens can be added to the designs to increase the scan angle. FIG. 8 schematically illustrates a distal portion 70 of an optical fiber scanner that includes a drum lens 72, which is attached to the distal end of a vibrating single mode optical fiber (not shown to simplify the drawing). Effective light source 74 for the light entering drum lens 72 is shown to be coincident with the vibratory node of the mechanical resonance. Converging light 80 emanates from the drum lens. A scan lens 76 focuses the light 82 on a curved image plane 78 in close proximity to the scan lens, as the drum lens rotates. FIG. 9 schematically illustrates a distal portion 90 of an optical fiber scanner in which parallel light 96 emanates from a GRIN lens 92 as the GRIN lens rotates about its back focal point 94 (also substantially coincident with the resonant node and effective light source of the vibrating optical fiber (not shown) to which the GRIN lens is attached). The parallel or collimated light is focused by a scan lens 98, producing light 100, which is incident on curved image plane 78. A scan lens of higher power is required to converge the light on an image plane of close proximity, compared to converging light emanating from the drum or GRIN lens that is more distant. When comparing optical beam scanning designs in accord with the present invention, increasing the degree of beam convergence emanating from the drum or GRIN lens enables an increased field of view and reduced axial length for the system.

Regarding FIGS. 8–9, if the light emanating from the optical fiber is converging, less scan lens power is needed to bring the light to a focus on a nearby image plane. If the light is collimated, more scan lens power is required. The increased power may come from the lens shape and/or a higher index of refraction of the glass used for the scan lens or lenses. The design of FIG. 8 has a lower refractive index scan lens. The exemplary design of FIG. 9 use higher refractive index scan lens. The exemplary designs of FIGS. 8 and 9 can handle scan angles of ±60°.

FIG. 10A illustrates a distal end 110 of an optical fiber 102, in an earlier (now prior art) scanner that is different than the present invention. In this scanner, a piezoelectric actuator 104 or other form of actuator causes optical fiber 102 to vibrate, so that distal end sweeps through an arc (as indicated by a distal end 110'). The distal end of the optical fiber comprises a point source that is scanned across an object plane 114 and is imaged by a magnifying lens 108 onto an illumination plane 116, for example creating a spiral scan pattern 112, enabling a time series photon detection. In contrast, the present invention, which is shown in FIG. 10B, includes an optical fiber 120, having a cantilevered portion that is substantially reduced in cross-sectional area. Optical fiber 120 is supported by piezoelectric actuator 104 and has a microlens 122 fused to its distal end that rotates when piezoelectric actuator 104 drives the optical fiber into a second resonance mode, to create a directed beam of illumination that is focused onto an illuminated region 126 with a scan lens 124, forming a spiral scan pattern 112'. In each of these optical fiber-scanners of FIGS. 10A and 10B, the backscattered light is detected with a single RGB photodiode detector 106, but alternatively, light can be collected by the same optical fiber in a confocal arrangement.

Recall that these exemplary designs assume no translation of the effective light source. The scan lens design can be modified to compensate for slight fluctuations of position of the lens that is affixed to the optical fiber during the scan. In addition, the optical fiber scanner can be moved to compensate for the small tip motion during a scan. Axial motion has been compensated using a Noliac piezoelectric ring bender to server as an axial actuator that provides a compensating axial movement.

The drum lens in the above noted exemplary design of FIG. 8 is modeled as a cylindrical piece of glass that is 0.125 mm in diameter by 0.87 mm long and is fused to the end of a single mode optical fiber that is 0.125 mm in diameter. Different sizes, shapes, or GRIN lens can be adhered to the optical fiber in these exemplary designs. Doublets, triplets, and GRIN lenses may be used in the external scan lens. All the exemplary designs discussed above were intended for use in compact endoscopes, with the image planes close to the lenses. However, it will be understood that these examples do not preclude the use of one or more external scan lenses to provide an image plane at much larger distances from the scanner.

Operation

The operation of an optical scanner micro-fabricated from an etched optical fiber is somewhat analogous to an optical scanner based on a mirror, in that the position of the resulting optical beam is a direct function of the position over time of the moving optical fiber or mirror. However, as mentioned above, the connection and alignment with the optical source or illuminating optical fiber is a simple and robust fiber-to-fiber connection resulting in >90% coupling efficiency. Whereas mirror-based optical scanners must have packaging that can maintain alignment and precise dimensional stability of a more complex optical system that includes an optical fiber holder and lenses, and must deal with the problems of multiple reflections and stray light, the present invention avoids these problems.

In operation, a piezoelectric bimorph or a tube actuator 142 in the present invention (see FIG. 11A) can accomplish the same scanning function as a moving mirror in the prior art. By applying an oscillating voltage to the piezoelectric material, the base of the micro-fabricated cantilevered waveguide is moved at a desired frequency. Although the piezoelectric bimorph is a one-dimensional (1-D) actuator and the tube is a 2-D or three-dimensional (3-D) actuator, two bimorphs can be assembled to provide 2-D actuation. A 2-D actuation of an optical fiber can produce resonant or non-resonant linear motion in two dimensions, and in several scanning patterns (rectilinear or raster pattern, circular or spiral pattern, rotating linear or propeller pattern, or other Lissajous patterns).

In a standard micro-image acquisition application, the light source is not electronically modulated to create sampled or pixelated images. Typically, the illuminated object has sufficient optical contrast (variable absorption, scattering, and topography) to modulate the backscattered and reflected light. One or more photon detectors (such as photodiode detector 106 in FIG. 10B) are required proximate the distal end of the optical fiber scanner to measure and temporally record the optical signal, which is synchronized with the waveguide position and displayed and/or stored accordingly. In commonly assigned U.S. Pat. No. 6,294,775, Seibel and Furness have outlined several embodiments and applications of scanned waveguide image acquisition systems. In all cases disclosed in this earlier patent, the size of the optical detectors do not determine the resolution of the acquired image.

To acquire (or display) a coherent image, the samples (or pixels) must be recorded (or output) from a buffer synchronized to the scanned light spot location or equivalently to the scanner (optical fiber tip and/or mirror) position. For example, in a raster display, it is important to start the output of a signal from a frame buffer when the scan is in an upper-left corner of the scanned field. In an acquisition system, the 2-D position of the scanned spot or scanner can be measured at the same moment that the intensity of the back-scattered light is measured with a photo detector. A time record of the position and intensity can be kept for each pixel in the image of the region being scanned. For each frame, after a sufficient time has elapsed, an image can be formed by taking the record of the position and intensity acquired for all the pixels that produce an image frame (an intensity map image). The scan does not need to be a periodic or repeatable scan. As long as the scan is space-filling within the duration of a frame, a complete coherent image will be captured.

In a display system, the 2-D position of the scanned spot or scanner can be measured and the desired pixel brightness at that location then found from a look-up table. The intensity of the laser light is then modulated to produce a pixel of desired brightness at the desired location. The scan does not need to be a periodic or repeatable scan. As long as the scan is space-filling within the duration of a frame, a complete coherent image will be formed.

It is possible to use open loop control by applying appropriate periodic drive signals (sinusoidal, square wave, etc.) to the actuator that vibrates the optical fiber, to produce stable periodic scan patterns. Acquired illumination samples (or output pixels) are correlated to assumed positions of the scan based on the relative time from a periodic reference sync signal related to the start of the frame acquisition (or display). Manual adjustment of relative phases of the scanner's drive signals, buffer input (or output), and sync signal, can be carried out to achieve stable coherent image acquisition (or display). These phases may need to be changed when scan amplitudes are changed (during a zoom), or environmental changes effect the scanner.

When zooming, the driver amplitude is reduced to decrease the field of view. Due to nonlinear effects, the phase relation between the drive and the output is not constant. If not accounted for, either by manual adjustment or by a lookup table, the image may become incoherent. Environmental changes may cause the resonant frequency of the optical fiber to change, also resulting in a phase and amplitude shift. These shifts can then be compensated by changing the amplitude and phase of the drive signals manually.

There are several advantages to using a circular scan. One of the advantages relates to tip mass. While the effect on an optical fiber with a tip mass has not been fully evaluated, based on what is known from work done with cylindrical and tapered optical fibers, it is likely that mass-tipped optical fibers vibrating in a circular scan will be less susceptible to jump than when vibrated in a 1-D sinusoidal scan; i.e., in a raster scan, because the frequency response curve of the circular scan does not change non-linearly as dramatically as the raster scan frequency response curve and therefore does not have multi-valued responses until much higher input amplitudes. In summary, a jump should occur at higher amplitudes with a circular scan than a raster scan, because the circular scan's frequency response curve does not change non-linearly as rapidly as other optical fiber scanning geometries.

For a spiral scan, the reference waveforms are horizontal and vertical sinusoid of the same frequency, but 90° out of phase; the amplitude of these waveforms have a saw tooth envelope with a frequency one-fourth the frame rate. In a spiral scan, the saw tooth envelope expands, contracts, expands, and contracts the sinusoid amplitude in each period. The relative phases are 0°, 0°, 180°, 180°. Computationally, these differences can be adjusted in apparent order of samples to achieve four frames per scan period. In other words, when the first expansion is the reference, the first contraction is flipped upside down, the second expansion is flipped right-to-left, and the second contraction is flipped upside down and right-to-left.

A final control method is proposed to reduce the small movement of the effective light source along the axis of the waveguide as a result of lateral bending of the waveguide during the vibratory scanning, as illustrated in FIG. 11A. Compared to when the waveguide is at a rest position 152, the effective light source moves proximally to a position 156 and further to a position 154, depending on the degree of waveguide bending. This small movement occurs because of the inextensibility of the waveguiding material. Electromechanical compensation can be performed using tube piezo actuator 142 in its axial expansion mode or by adding a separate axial actuator 160. As illustrated in FIG. 11B, axially moving the waveguide distally so that the effective light source moves distally to compensate for the normal axial movement as a function of bending amplitude, the effective light source can be maintained substantially coincident to the vibratory node, as shown by a dotted vertical line in FIG. 11B. The range of axial movement is small, (e.g., between point 154 and point 156 as a function of the amplitude of the incremental lateral motion of the waveguide), so that the piezoelectric actuators of a tube or ring bender can be used in a non-resonance mode to compensate the axial movement.

A lead 144 conveys drive signals to actuator tube 142 to drive it so that it moves the cantilevered portion of the optical fiber in a desired pattern at a desired frequency, as determined by a light source and controller 146. In one embodiment, a scanning waveguide with a microlens at the distal tip has ideal optical properties if the optical beam appears to come from a single fixed point. In this case, the axial position of the lensed waveguide is adjusted to compensate for a moving effective light source during the scan. As shown in FIG. 11A, the axial position of the waveguide can be adjusted with piezo actuator tube 142, which is made from piezoelectric material, which can be moved in three axes (2-D for laterally scanning and axially for improving the optical performance), or in a second embodiment shown in FIG. 11B, by using separate axial actuator 160 (e.g., piezoelectric, electrostrictive, or magnetostrictive) to move the piezoelectric tube actuator and optical fiber axially. Axial actuator 160 is anchored to a supporting structure (not shown) used to introduce the optical fiber scanner into a desired location, and a scan lens (also not shown) is also anchored to the supporting structure.

FIGS. 12A–12C illustrate how the effective light source moves along divergent paths relative to a resonant node during vibration of an optical fiber 170 in a linear scan, for the present invention, as a result of the axial sliding that occurs because the optical fiber is incompressible along the axis of the optical fiber. Small circles 172 correspond to different exemplary positions of the effective light source as optical fiber 170 vibrates through several positions during a cycle. A track 174 shows the movement of the effective light source at these different positions. Sequentially, the effective light source moves relative to the node first along a track 174a, followed by a track 174b, followed by a track 174c, and then by a track 174d, before repeating these tracks during the next cycle. Ideally, it would be preferable to minimize the lateral deflections of the effective light source. Axial deflections of the effective light source are compensated as noted above in regard to FIGS. 11A and 11B.

FIGS. 12D–12F, again for a linear scan, illustrate how by moving the effective light source further toward the distal end than the resonant node (relative to its nominal position when the optical fiber is at rest), the lateral deflection of the effective light source is substantially reduced compared to that shown in FIGS. 12A–12C. In this case, an optical fiber 176 has an effective light source that moves along a track 180, as indicated by the positions of circles 178 (FIG. 12D). During each cycle of vibration of optical fiber 176, the effective light source moves along a track 180a, followed by a track 180b, followed by a track 180c, and then by a track 180d. Clearly, the lateral deviation of these tracks are much reduced, compared to tracks 174a–174d.

Therefore, due to the inextensibility of the fiber scanner, maintaining alignment of the vibratory node with the distal end of the waveguide (i.e., the effective light source for the fused optical element) is an engineering challenge. Efforts to maintain this alignment while scanning will be deemed necessary only if the resulting image quality is significantly degraded when scan amplitude is varied.

ALTERNATIVE EMBODIMENT

FIG. 13 illustrates an alternative embodiment of an optical beam scanner 188 in accord with the present invention. In this embodiment, tube piezo actuator 142 (or another suitable actuator) is used to excite a bending waveguide 190 to move in a desired pattern and amplitude, and at a desired frequency. The dash lines show the corresponding shape and disposition of the bending waveguide when it is displaced 180 degrees in phase. Preferably, the portion of bending waveguide 190 that is thus excited into motion will be reduced in cross-sectional area, as described above, to enhance the flexibility of the waveguide in this region.

Light is conveyed through a core 192 of bending waveguide 190 toward its distal end, where an optical component 196, such as a drum (barrel) lens, or GRIN lens, or diffractive optical element is attached. In this embodiment, when thus excited, the bending waveguide has a vibratory node 194 that is substantially proximal of an effective light source 198. Because of the displacement of vibratory node 194 from effective light source 198, scanning occurs primarily due to the rotation of the optical component, but also due to the translation of the optical component and distal end of bending waveguide 190. Light 202 emitted from optical component 196 is slightly convergent and is focused by a scan lens 200 to produce focused light 204 that converges to a focal point 206. Movement of bending waveguide 190 thus causes effective light source 198 to move through a translation distance 208 and rotates the focused light generally through an upper rotational distance 210a and a lower rotational distance 210b (neither to scale). The scanning of focal point 206 for optical beam scanner

188 thus results primarily from the rotation of the optical component, but also to a lesser extent, from the translation of the effective light source.

Contemplated Modifications

Use of other waveguide materials that are more elastic might result in a reduction of the axial translation of the optical source during scanning and yield an improved optical quality for the system.

The micro-fabricated waveguide can be an optical fiber made from any transparent material suitable for the particular wavelength of electromagnetic radiation that is to be scanned. For the near ultraviolet (UV), visible, and near infrared wavelengths, the most common optical materials will be fused silica, quartz, sapphire, glasses, and clear plastics and polymer rubbers (for example PMMA (polymethylmethacrylate) and PDMS (poly(dimethylsiloxane)). The optical fiber does not have to rely on total internal reflection to guide the electromagnetic radiation. For example, hollow tubes and tapered pipettes can be used that rely on oblique-angle reflection at high efficiencies. Photonic crystal fibers also use a mechanism for wave guiding that is different from total internal reflection. Reflection from metallic surfaces is another embodiment.

In an alternative scanner configuration that does not use an optical waveguide, a cantilever can be made from any material that is not a waveguide, as long as the tip contains an effective light source that can be moved, scanned, or vibrated into a high displacement or high deflection angle. Most likely the cantilever would contain the leads to a light source micro-fabricated at the optical fiber distal tip, such as a micro-LED (light emitting diode), nanolaser, or vertical-cavity surface-emitting laser (VCSEL). However, this effective light source could be a micro-mirror that re-directs a beam of light or that scatters light to create an effective light source position from being illuminated by incident radiation. The incident energy source that excites and possibly drives the scanner in motion does not have to be of the same form as the light output, e.g. microwave radiation or ultrasonic energy might be used to generate the scanning light source.

The micro-machined cantilever waveguide can be used as a scanning optical detector in addition to or instead of a scanning optical illuminator. Thus, a photodetector might replace the micro light source at the tip of a non-transmissive scanning cantilever.

Mechanical resonance is not required for all embodiments and applications of these devices. For example, a cantilever that is scanned at non-resonant frequencies may be preferred for optical switching applications.

Micro-fabricating of waveguides and the micro-optical fabrication of lenses, as well as the operation of the devices do not have to be done one-at-a-time, but can also be made and used in parallel. For example, the micro-fabricated waveguide scanning devices can be made by batch processing, whereby they are created, assembled, processed, and/or used in linear, 2-D, and 3-D arrays. Processes used for micro-fabricating MEMS and IC devices are applicable.

The operation of the optical fiber optical scanner may be done in parallel or in an array format. Thus, field of view and scan frequency requirements may be reduced.

The methods of micro-fabrication and micromachining are not limited to methods that remove or simply redistribute waveguide material. Additional waveguide material can be added by crystal growth, vapor, sputter, and chemical deposition, gluing, bonding, welding, etc.

The method of acid etching can be modified by etching the waveguide in solutions of more than three layers of different solutions (such as an additional layer of organic liquid, or in baths that contain gradients of pH, acid concentration, or solute diffusion coefficients. The etching process can be influenced by confining the waveguide in a tube or other physical barrier that affects the etching rates axially and laterally along the waveguide.

The method of etching can also be modified by using surface charge effects or relative hydrophobicity of waveguide surfaces to aid in reducing the etchant layer depth (which determines the length of the diameter-reduced region on the optical fiber).

In addition to static etch layers, the method of etching can further be modified to include flowing liquid acids or other solvents or vapors or abrasives that may vary in concentration or flow rate during the etching process.

The method of etching can be varied by first coating the waveguides with a layer that may have a graded or predetermined pattern of protection from etching, such as a layer of a photo resist that has been exposed differentially to polymerization.

The method of etching can alternatively include vapor etching, plasma etching, laser etching, electrolytic etching, liquid slurry etching, air-particulate erosion, and mechanical polishing and beveling.

The method of micro-optical lens fabrication can include single and repeated applications of UV-cure or heat-cure optical adhesives of various amounts, refractive indices, viscosities, hydrophobicities, adhesion properties, etc.

The method of micro-optical lens fabrication can include the attachment and bonding of spacers, sleeves (hollow tubes), microlenses (refractive lenses, gradient index lenses, and/or diffractive optical elements), micro-diffusers, etc. Attachment methods include fusion-splicing or epoxy.

The method of mechanically actuating the micro-fabricated waveguide into vibratory motion (resonant or non-resonant) can include the use of piezoelectric, electromechanical, electrothermal, opto-thermal, electromagnetic, galvanomeric, magnetostriction, ultrasonic, electrostriction, and electrostatic actuators from either base, side, and/or tip of the waveguide.

The optical fiber scanner with a microlens can include strain sensors, optical bending sensors, polarization sensors, piezoelectric thin film sensors for feedback control of the scanner dynamics. In addition, the optical fiber scanner can include magnetic or ferrous materials for magnetic sensing of scanner motion, stabilizing motion such as "pinning" the stationary lens, or actuating the optical fiber of the scanner into motion. The optical fiber scanner and or microlens can be coated with metal or piezoelectric for electrostatic/electromechanical sensing or actuation.

The optical fiber scanner with a microlens can be constructed from one or more concentric waveguides. For example, a central solid or hollow core can be used for illumination while the surrounding ring waveguide is used for collecting an optical signal for feedback control or for conveying a backscattered, fluorescence, or coherent imaging signal.

Although the present invention has been described in connection with the preferred form of practicing it and modifications thereto, those of ordinary skill in the art will understand that many other modifications can be made to the present invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for fabricating a compact optical scanner for scanning a region, comprising the steps of:
   (a) providing a waveguide through which light is guided between a proximal end and a distal end of the waveguide;
   (b) attaching an optical component to the distal end of the waveguide, said optical component having a back focal plane;
   (c) substantially reducing a cross-sectional area of a portion of the waveguide adjacent to the distal end, leaving the distal end of the waveguide where the optical component is attached unreduced in cross-sectional area; and
   (d) coupling an actuator to the waveguide to vibrate the portion of waveguide that is reduced in cross-sectional area at a desired frequency and in a desired pattern, excitation of the waveguide by the actuator causing the optical component to rotate without substantial lateral displacement, so as to scan a region with light exiting the optical component, wherein a characteristic of the light emitted from the optical component is selectively determined by controlling a spatial relationship between the effective light source position and at least one of:
   (i) a back focal point of the optical component; and
   (ii) a location of a vibratory node of the portion of the waveguide that is cantilevered from the actuator.

2. The method of claim 1, wherein the step of substantially reducing a cross-sectional area of a portion of the waveguide comprises the step of immersing the waveguide in a multi-layer etching apparatus that includes an etchant layer of a liquid selected for its ability to etch away material comprising the waveguide to reduce the cross-sectional area of the waveguide when the waveguide is exposed to the etchant layer.

3. The method of claim 2, wherein the multi-layer etchant apparatus includes a solvent layer disposed above the etchant layer and an etch-stop layer disposed below the etchant layer, said optical component being immersed within said etch-stop layer when the portion of the waveguide is immersed in the etchant layer to reduce the cross-sectional area of said portion of the waveguide.

4. The method of claim 3, wherein the solvent layer prevents vapors from the etchant layer from attacking the waveguide above the etchant layer.

5. The method of claim 3, wherein the etch-stop layer comprises a fluorinated oil that stops the liquid of the etchant layer from etching away the material comprising the waveguide and the optical component, once the waveguide and optical component are immersed within the etch-stop layer.

6. The method of claim 1, wherein the etchant layer comprises hydrofluoric acid.

7. The method of claim 1, wherein the step of attaching the optical component to the distal end of the waveguide comprises the step of fusing the optical component to the waveguide by employing a source of energy to heat the distal end of the waveguide.

8. The method of claim 1, wherein the optical component comprises a drum lens, further comprising the step of modifying a distal surface of the drum lens to optically focus light exiting the optical component so that the light travels in one of a substantially collimated path and a converging path.

9. The method of claim 1, further comprising the step of providing one of a ball lens, a drum lens, a graded index (GRIN) lens, and a diffractive optical element as the optical component attached to the distal end of the waveguide.

10. The method of claim 1, wherein the step of substantially reducing the cross-sectional area of the waveguide comprises the step of selecting dimensions of said portion and of a part of the waveguide that is adjacent to and distal of said portion, to ensure that a vibratory node of waveguide, when driven into vibration by the actuator, is substantially coincident with the back focal plane of the optical component.

11. The method of claim 1, wherein the optical component includes a back focal plane, and wherein the waveguide includes an effective light source at a position adjacent to the distal end of the waveguide where the waveguide has substantially reduced wave guiding capability, said step of attaching the optical component comprising the step of positioning the effective light source substantially coincident with the back focal plane of the optical component.

12. The method of claim 1, wherein the optical component includes a back focal plane, and wherein the waveguide includes an effective light source at a position adjacent to the distal end of the waveguide where the waveguide has substantially reduced wave guiding capability, said step of attaching the optical component comprising the step of positioning the effective light source proximal to the back focal plane of the optical component.

13. The method of claim 1, wherein the step of attaching the optical component to the distal end of the waveguide substantially reduces a wave guiding capability of the waveguide at an effective light source position, said effective light source position being substantially coincident with the vibratory node of the waveguide.

14. The method of claim 13, further comprising the step of providing an axial actuator for axially moving the waveguide in synchrony with the vibration of the waveguide so as to compensate for a variation in an axial position of the effective light source position of the light conveyed by the waveguide caused by a deflection of the portion of the waveguide that is reduced in cross-sectional area.

15. The method of claim 1, wherein the step of substantially reducing the cross-sectional area of a portion of the waveguide adjacent to the distal end comprises the step of forming a desired non-linear shape for the waveguide in the portion where the cross-sectional area is substantially reduced.

* * * * *

UNITED STATES PATENT AND TRADEMARK OFFICE
CERTIFICATE OF CORRECTION

PATENT NO. : 6,959,130 B2
DATED : October 25, 2005
INVENTOR(S) : Fauver et al.

It is certified that error appears in the above-identified patent and that said Letters Patent is hereby corrected as shown below:

Column 1,
Line 13, insert the following:
-- Government Rights
This invention was funded at least in part with grant No. 9978888 from the National Science Foundation (NSF), and the U.S. government may have certain rights. --.

Signed and Sealed this

Twenty-first Day of March, 2006

JON W. DUDAS
*Director of the United States Patent and Trademark Office*